(12) United States Patent
Ario et al.

(10) Patent No.: US 6,537,547 B1
(45) Date of Patent: Mar. 25, 2003

(54) POLYPEPTIDES HAVING L-ASPARAGINASE ACTIVITY

(75) Inventors: Takeshi Ario, Okayama (JP); Madoka Taniai, Okayama (JP); Kozo Yamamoto, Okayama (JP); Masashi Kurimoto, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 08/869,927

(22) Filed: Jun. 5, 1997

(30) Foreign Application Priority Data

Jun. 7, 1996  (JP) .............................................. 8-168172

(51) Int. Cl.⁷ ........................... A61K 38/46; C12N 9/82
(52) U.S. Cl. ...................................... 424/94.6; 435/229
(58) Field of Search ................................ 435/229, 228, 435/227; 424/94.6; 536/23.2, 23.5

(56) References Cited

FOREIGN PATENT DOCUMENTS

| EP | 0 726 313 A2 | 8/1996 |
|----|--------------|--------|
| JP | 119082/79 | 9/1979 |
| JP | 19018/80 | 2/1980 |
| JP | 320684/92 | 11/1992 |

OTHER PUBLICATIONS

Yellin et al. "Purification and properties of guinea pig serum asparaginase" Biochemistry 5, 1605–1612, May 1966.*
Patent Abstracts of Japan, vol. 17, No. 158 (C–1041) (1993): abstract of JP 04 320684 of Nov. 11, 1992.
Ausubel et al (Eds.), *Current Protocols in Molecular Biology*, vol. 1, John Wiley & Sons, Inc. (1995), pp. iii–xi; 9.0.1–9.0.3; 9.2.1–9.2.6.
Broome, J.D., Evidence that the L–Asparaginase Activity of Guinea Pig Serum is responsible for its Antilymphoma Effects, *Nature* 191:1114 (1961).
Harmes et al, A catalytic role for threonine–12 of *E. coli* asparaginase II as established by site–directed mutagenesis, *FEBS* 285(1):55–58 (1991).
Hay et al (Eds.), *ATTC Cell Lines and Hybridomas*, 8th Ed., American Type Culture Collection, Rockville, MD; pp. ii, iv, 150, 152, 159 (1994).
Horton et al, "Gene Splicing by Overlap Extension", *Methods in Enzymology*, 217:270–279 (1993).
Kidd, J. G., "Regression of Transplanted Lymphomas Induced in Vivo by Means of Normal Guinea Pig Serum", *The Journal of Experimental Medicine* 98:565–583 (1953).
Kozak, M., "An analysis of 5'–noncoding sequences from 699 vertebrate messenger RNAs", *Nucleic Acids Research* 15(20):8125–8148 (1987).
Laemmli, U.K., "Cleavage of Structural Proteins during the Assembly of the Head of Bacteriophage T4", *Nature* 277:680–685 (1970).
Sambrook et al, *Molecular Cloning: A Laboratory Manual*, Cold Spring Harbor Laboratory Press, (Cold Spring Harbor, NY, 1989), pp. xi–xxxviii.
Stern et al, "Construction of a Novel Oncogene Based on Synthetic Sequences Encoding Epidermal Growth Factor", *Science* 235:321–324 (1987).
Towbin et al, "Electrophoretic transfer of proteins from polyacrylamide gels to nitrocellulose shets: Procedure and some applications", *PNAS, USA* 76(9):4350–4354 (1979).

* cited by examiner

*Primary Examiner*—Nashaat T. Nashed
(74) *Attorney, Agent, or Firm*—Browdy And Neimark

(57) ABSTRACT

Disclosed are polypeptides which originate from mammal, having L-asparaginase activity. The polypeptides are easily prepared by applying recombinant DNA techniques to DNAs encoding the polypeptides and they exert satisfactory effects in the treatment and/or the prevention for diseases caused by tumor cells dependent on L-asparagine, and cause no substantial serious side effects even when administered to humans in relatively-high dose.

5 Claims, 8 Drawing Sheets

FIG. 1
DNA with an original nucleotide sequence
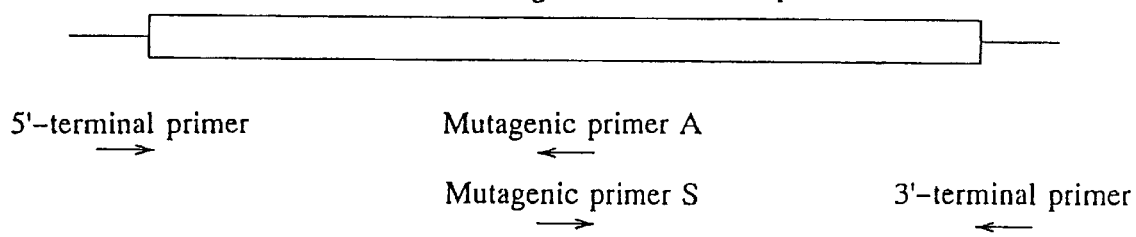
[First step PCRs]
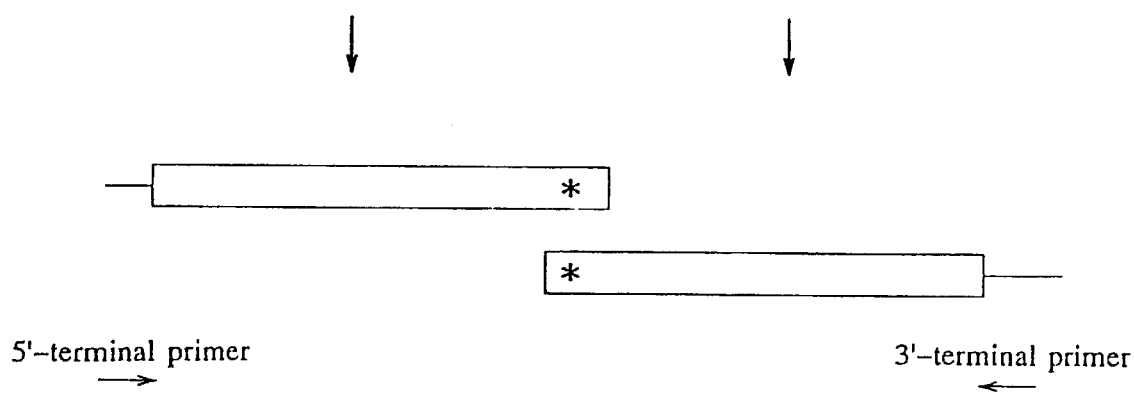
[Second step PCR]
↓
DNA homologue
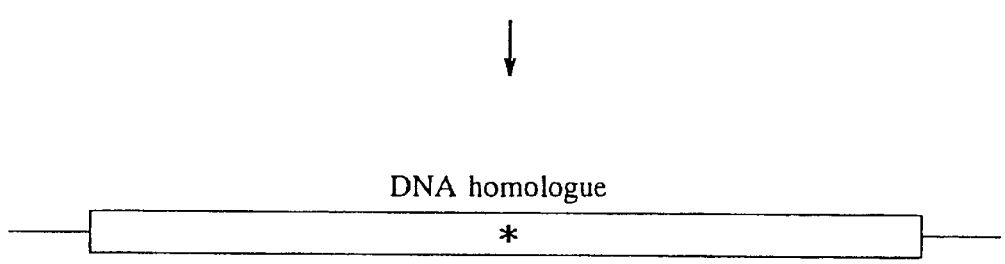
Note: An asterisk indicates a site where a nucleotide is substituted, and a box indicates a polypeptide-encoding sequence.

```
Template DNA       : pCGPA/WT
Sense primer       : 5'-GTGAATTCGGAGGTTCAGATGGCGCGCGCATCA-3'
Anti-sense primer  : 5'-CTGCGGCCGCTCAGATGGCAGGCGGCAC-3'
                    ↓ PCR
            Amplified DNA
                    ↓ Cleavage by Eco RI and Not I
      DNA fragment about 1.7 kbp in length
```

```
Linkers :
5'-TCGAGCCACCATGAAGTGTTCGTGGGTTATT-3'
5'-TTCTTCCTGATGGCCGTAGTGACAGGAGTG-3'
5'-AATTCACTCCTGTCACTACGGCCATCAGGA-3'
5'-AGAAAATAACCCACGAACACTTCATGGTGGC-3'
            ↓ Phoshporylation
              by T4 polynucleotide kinase
5'-terminal phosphorylated linkers
```

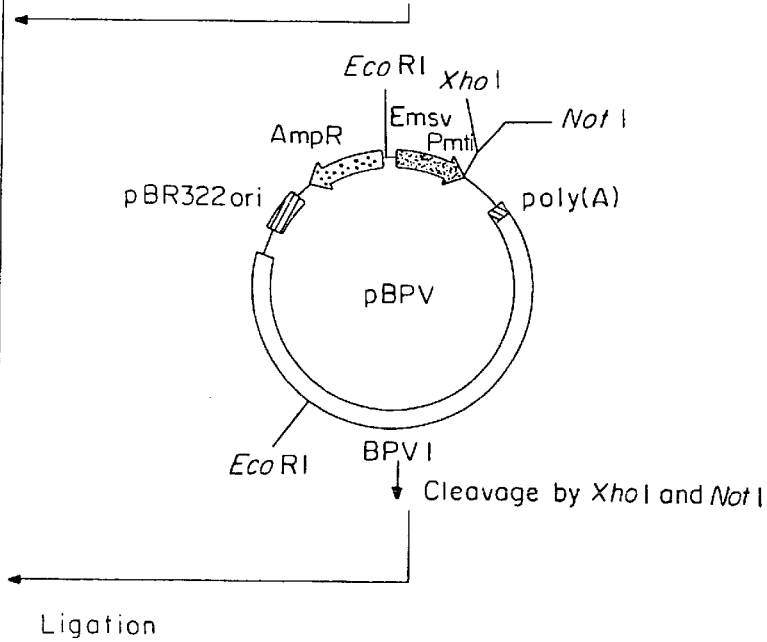

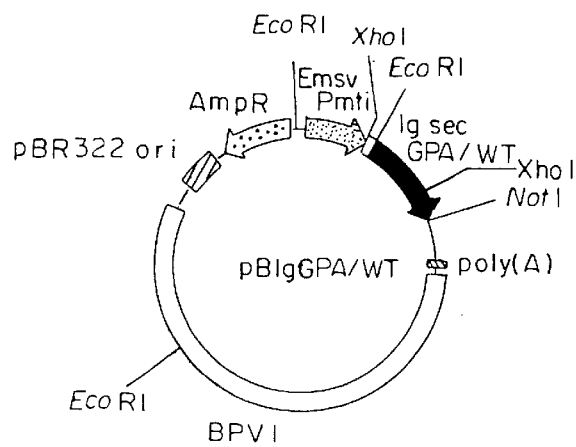

FIG. 3

POLYPEPTIDES HAVING L-ASPARAGINASE ACTIVITY

BACKGROUND OF THE INVENTION

1. Field of the Invention

The present invention relates to L-asparagine amidohydrolytic enzymes, more particularly, to polypeptides which originate from mammal, having L-asparaginase activity.

2. Description of the Prior Art

L-Asparaginase (EC 3.5.1.1) is an enzyme which catalyzes the hydrolytic reaction of L-asparagine into L-aspartic acid and ammonia. The studies on the antitumor activity of L-asparaginase started from the following reports: J. G. Kidd et al. described the inhibitory action of guinea pig sera on cells of lymphomas in "The Journal of Experimental Medicine", Vol.98, pp.565–582 (1953), and J. D. Broome et al. evidenced in "Nature", Vol.191, pp.1,114–1,115 (1961), that the L-asparaginase activity of the guinea pig sera was responsible for the inhibitory action. It is now understood that the inhibitory action is caused by the lack of L-asparagine, an essential nutrient to proliferate and survive for some tumor cells which defect L-asparagine synthetase activity, such as acute lymphocytic leukemia, but not for normal cells. The hydrolysis of L-asparagine by L-asparaginase in patients with such tumor cells induces selective death of the tumor cells, resulting in the treatment of malignant tumors.

L-Asparaginase has been studied energetically for its actual use as an antitumor agent, and one derived from *Escherichia coli* is now in use as a therapeutic agent for leukemia and lymphoma. However, L-asparaginase from *Escherichia coli* is merely an external protein for human, and repetitive administration of conventional compositions with such L-asparaginase may cause serious side effects such as anaphylaxis shock, urticaria, edema, wheeze and dyspnea. These compositions are inevitably restricted with respect to administration dose and frequency. Therefore, some proposals to reduce or even diminish such side effects have been given.

As a first proposal, Japanese Patent Kokai No.119,082/79 discloses a chemically modified L-asparaginase from *Escherichia coli*, in which at least 65% amino acids are blocked with 2-O- substituted polyethylene glycol-4,6-dichloro-S-triazine. As a second proposal, human L-asparaginases are disclosed in Japanese Patent Kokai Nos.320,684/92 and 19,018/80, where the L-asparaginases are respectively obtained from cultures of human cell lines and human urine. While the first proposal has an advantage of that the L-asparaginase from *Escherichia coil* is easily obtainable on an industrial scale, it has a disadvantage of that the modifying reaction is difficult to control and the side effects couldn't be eliminated completely. While the second proposal has an advantage of that unlike L-asparaginase from *Escherichia coli*, the L-asparaginases from human may not substantially induce antibodies even when administered to patients, it has a disadvantage of that it is not easy to obtain the L-asparaginases in a desired amount by the processes disclosed in Japanese Patent Kokai Nos.320,684/92 and 19,018/80.

Recently, recombinant DNA technology has advanced remarkably. If a DNA which encodes a desired polypeptide is once isolated, it is relatively easy to obtain a transformant which produces the polypeptide by constructing a recombinant DNA, comprising the DNA and a self-replicable vector, followed by introducing the recombinant DNA into a host, such as a microorganism, animal- or plant-cell. The polypeptide is obtainable in a desired amount from the culture of the transformant. However, no DNA which encodes mammalian L-asparaginase was isolated, and no mammalian L-asparaginase was produced by recombinant DNA techniques.

Therefore, it has been in great demand to isolate DNAs which encode active L-asparaginases originating from mammal and establish processes to prepare the L-asparaginases on a large-scale by applying the recombinant DNA techniques to the isolated DNAs.

SUMMARY OF THE INVENTION

In view of foregoing, the first object of the present invention is to provide a polypeptide which originates from mamma, having L-asparaginase activity.

The second object of the present invention is to provide a DNA which encodes the polypeptide.

The third object of the present invention is to provide a recombinant DNA which containing a DNA which encodes the polypeptide and a self-replicable vector.

The fourth object of the present invention is to provide a transformant obtainable by introducing a DNA which encodes the polypeptide into a host.

The fifth object of the present invention is to provide a process to prepare the polypeptide by using the transformant.

The sixth object of the present invention is to provide an agent for susceptive diseases, containing the polypeptide as an effective ingredient.

The first object of the present invention is attained by polypeptides which originate from mammal, having L-asparaginase activity.

The second object of the present invention is attained by DNAs which encode the polypeptides.

The third object of the present invention is attained by recombinant DNAs containing DNA which encode the polypeptides and a self-replicable vector.

The fourth object of the present invention is attained by transformants obtainable by introducing the DNAs into appropriate hosts.

The fifth object of the present invention is attained by a process to prepare the polypeptides which comprises culturing the transformants and collecting the produced polypeptides from the resultant cultures.

The sixth object of the present invention is attained by agents for susceptive diseases, containing the polypeptides as effective ingredients.

BRIEF EXPLANATION OF THE ACCOMPANYING DRAWINGS

FIG. 1 is a scheme of the over lap extension method.

FIG. 3 is a scheme of the preparation of the recombinant DNA pBIgGPA/WT.

Figure 2:
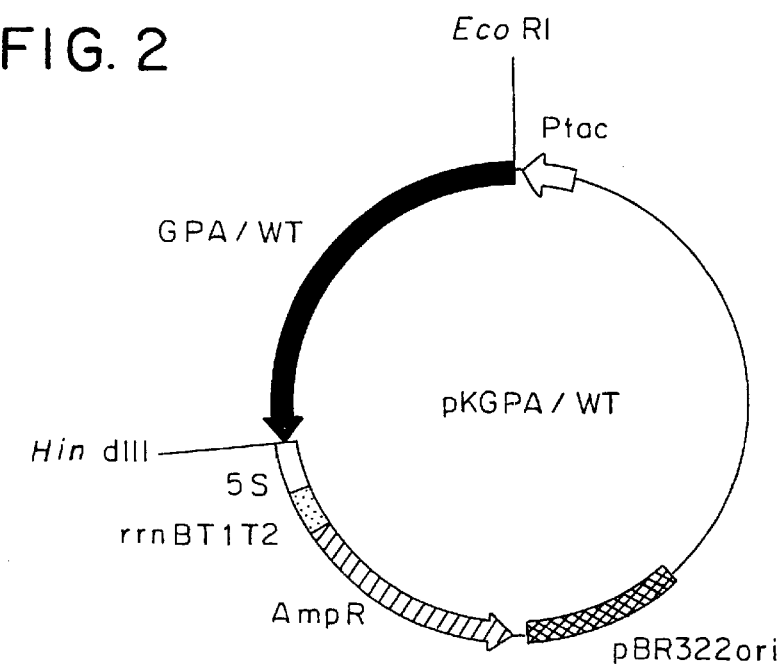
FIG. 2 is a restriction map of recombinant DNA pKGPA/WT.

Explanation of the symbols are as follows:

The symbols, "Eco RI", "Hin dIII", "Not I" and "Xho I", indicate cleavage sites by restriction enzymes, Eco RI, Hin dIII, Not I and Xho I, respectively.

The symbols, "D364stp", "HA/MUT1", "HA/MUT2", "HA/MUT3" and "HA/MUT5", indicate DNAs encoding the present polypeptides.

The symbol "Ptac" indicates a Tac promotor.

The symbol "rrnBT1T2" indicates a region for transcriptional termination, derived from a ribosomal RNA operon.

The symbol "AmpR" indicates an ampicillin resistant gene.

The symbol "pBR322ori" indicates a replication origin in *Escherichia coli*.

The symbol "Ig sec" indicates a DNA encoding a polypeptide with a signal sequence for secretion of immunoglobulin.

The symbol "Emsv" indicates an enhancer from long terminal repeats of Moloney Mouse Sarcoma Virus.

The symbol "Pmti" indicates a promotor for Mouse metallothionein I gene.

The symbol "Poly (A)" indicates a polyadenylation signal derived from SV40 virus.

The symbol "BPVI" indicates a genome of a bovine papillomavirus.

DETAILED DESCRIPTION OF THE INVENTION

The present inventors isolated mammalian DNAs encoding L-asparaginases firstly in the world, from guinea pig and human, and succeeded in elucidating their nucleotide sequences. The nucleotide sequences of the DNAs from a guinea pig and human are in SEQ ID NOs:15 and 16, respectively. This information is disclosed in Japanese Patent Application No.42,564/95 (Japanese Patent Kokai No.214,885/96) by the same applicant of this application. The present invention has been made based on the above information, and provides the polypeptides which originate from mammal, having L-asparaginase activity.

The polypeptides of the present invention are not restricted to their sources or origins so far as they originate from mammal and have an L-asparaginase activity. The polypeptides are usually obtainable by the expression of genes originating from mammal, and usually contain amino acid sequences of SEQ ID NOs:1 to 3, wherein the symbol "Xaa" in SEQ ID NO:3 means "glutamine" or "arginine". For example, the polypeptides have any one of amino acid sequences of SEQ ID NOs:4 to 9. In view of the technical level in this field, one or more amino acid residues in SEQ ID NOs:4 to 9 can be substituted relatively easily by different ones without substantial defects of the activity. Despite derived from the same DNA, a variety of polypeptides with an L-asparaginase activity may be obtained as a result of modifications by endogenous enzymes of the hosts after the DNA expression or modifications during purification of the polypeptides, depending on the types of vectors and hosts used to obtain transformants or culturing conditions of the transformants, such as ingredients, compositions, temperatures or pHs. The wording "a variety of polypeptides" includes the polypeptides with deletions and/or additions of one or more amino acids at the N-and/or C-termini thereof, or with glycosylations. In view of these, the present polypeptides include not only the polypeptide with any amino acid sequence of SEQ ID NOs:4 to 9 but also their homologues so long as they have an L-asparaginase activity. The present polypeptides express the activity when exist in multiple forms, preferably, tetramers.

The polypeptides of the present invention can be usually prepared by the recombinant DNA techniques. In general, the polypeptides are obtainable by culturing transformants containing DNAs encoding the polypeptides and collecting the produced polypeptides from the resultant cultures. The transformants are obtainable by introducing such recombinant DNAs as contain any one of the nucleotide sequences of SEQ ID Nos:10 to 15 and a self-replicable vector into appropriate hosts. One or more nucleotides in SEQ ID NOs:10 to 15 can be substituted by different nucleotides without substantial changes of the encoding amino acid sequences with respect to degeneracy of genetic code. To facilitate the expression of the DNA in the hosts, one or more nucleotides in nucleotide sequences which encode the polypeptides or their homologues can be appropriately substituted by different ones. Furthermore, nucleotide sequences which encode and/or don't encode one or more amino acids can be added to the 5'- and/or 3'-termini of the nucleotide sequences.

The DNAs encoding the polypeptides of this invention include those from natural sources and those by synthesized artificially so far as the polypeptides expressed by them have an L-asparaginase activity. The DNAs can be wild-type ones, containing the same nucleotide sequences as those from natural sources, and can be their homologues.

Examples of the wild-type DNAs include DNAs containing the nucleotide sequences of SEQ ID NOs:15. The wild-type DNA is obtainable from natural sources such as guinea pig livers, as disclosed in Japanese Patent Application No.42,564/95 (Japanese Patent Kokai No.214,885/96) by the same applicant of this invention: (a) constructing a cDNA library by applying usual methods to purified poly (A)⁺ RNAs from a guinea pig or human liver as materials, (b) applying the plaque hybridization method to the cDNA library using oligonucleotides as probes synthesized chemically based on partial amino acid sequences of L-asparaginase purified from a guinea pig serum, (c) collecting phage clones containing the DNAs encoding the polypeptides of this invention, and (d) manipulating the collected phage clones in a conventional manner. The wild-type DNA can be synthesized chemically based on SEQ ID NO:15.

Examples of DNA homologues to the wild-type ones include DNAs containing any nucleotide sequence of SEQ ID NOs:10 to 14. DNA homologues containing the nucleotide sequence of SEQ ID NO:10 are obtainable by applying conventional methods in this field, such as PCR method and methods for site-directed mutagenesis, to the wild-type DNA of SEQ ID NO:15 concerning the desired sequence.

DNA homologues containing any nucleotide sequence of SEQ ID NOs:11 to 14 are obtainable by the methods such as follows: Firstly, A wild-type DNA with the nucleotide sequence of SEQ ID NO:16 obtained by the methods as disclosed in Japanese Patent Application No.42,564/95 (Japanese Patent Kokai No.214,885/96) by the same applicant of this invention, i.e., screening a human liver cDNA library. Subsequently, the wild-type DNA is subjected to conventional methods as mentioned above concerning desired sequences to obtain the DNA homologues. The DNA homologues can be synthesized chemically based on the nucleotide sequences of SEQ ID NOs:10 to 14.

The present DNAs can be generally introduced into hosts as in forms of recombinant DNAs. In general, each recombinant DNA comprises one of the present DNAs and a self-replicable vector. The recombinant DNAs can be easily prepared by general recombinant DNA techniques when the DNAs are available. Examples of such self-replicable vectors include pKK223-3, pGEX-2T, pRL-λ, pBTrp2 DNA, pUB110, YEp13, Ti plasmid, Ri plasmid, pBI121, pCDM8, pBPV and BCMGSneo. Among these vectors, pKK223-3, pGEX-2T, pRL-λ, pBTrp2 DNA pUB110 are suitably used to express the present DNAs in prokaryotic cells such as *Escherichia coli* and Bacillus sp., while YEp13, Ti plasmid, Ri plasmid, pBI121, pCDM8, pBPV and BCMGSneo are suitably used to express the present DNAs in eukaryotic cells such as yeasts and animal- and plant-cells.

To insert the present DNAs into the vectors, conventional methods in this field can be arbitrarily used. Examples of such methods contain the steps of (a) cleaving self-replicable vectors with restriction enzymes, (b) introducing the same cleavage sites, by the same restriction enzymes as used to cleave the vectors, to the 5'- and 3'-termini of the present DNAs by applying polymerase chain reaction to form double-stranded DNAs, (c) cleaving the double-stranded DNAs by the restriction enzymes, and (d) ligating the cleaved vectors with cleaved DNAs by the action of DNA ligases. The recombinant DNAs thus obtained can be easily introduced into appropriate hosts, resulting in limitless replication of the DNAs by culturing the transformants.

The recombinant DNAs according to the present invention can be introduced into appropriate hosts such as *Escherichia coli*, Bacillus sp., actinomycetes, yeasts and plant-and animal-cells. To introduce the DNAs into *Escherichia coli*, it can be cultured in the presence of the recombinant DNAs and calcium ion. To introduce them into Bacillus sp., competent cell methods or protoplast methods can be used. To introduce them into animal-cells, DEAE-dextran methods or electroporation methods can be used. Desired transformants can be cloned by applying hybridization methods or by selecting L-asparaginase producing cells from the cultures.

The transformants thus obtained produce the present polypeptides intracellularly or extracellularly when cultured in nutrient culture media. Examples of such media are usually liquid nutrient culture media which generally contain carbon sources, nitrogen sources and minerals, and further contain micronutrients such as amino acids and/or vitamins on demand. The carbon sources usable in the present invention include saccharides such as starch, starch hydrolysates, glucose, fructose and sucrose. The nitrogen sources usable in the present invention include organic and inorganic compounds containing nitrogen, such as ammonia and their salts, urea, nitrates, peptone, yeast extract, defatted soy bean, corn steep liquor and beef extract. Cultures containing the present polypeptides can be obtained by inoculating the transformants into the above media, culturing them at temperatures of 25–65°C. at pHs of 5–8 for about 1–10 days under aerobic conditions by aeration-agitation method, etc.

The cultures can be used intact as agents for susceptive diseases. However, the cultures are usually treated with ultrasonication or cell wall lytic enzymes to disrupt cells, and the present polypeptides are separated by using techniques such as filtration and centrifugation from the cell-disruptants and purified. Alternatively, the polypeptides can be purified from the culture supernatants obtained by removing cells from the cultures by filtration or centrifugation, etc. The present polypeptides can be purified by applying techniques generally used in this field for protein purifications, such as salting out, dialysis, filtration, concentration, gel filtration chromatography, ion-exchange chromatography, affinity chromatography, hydrophobic chromatography, isoelectric focusing and gel electrophoresis, and if necessary, two or more of them can be applied combination to the supernatants which are separated from insoluble substances of cell-disruptants, or to the culture supernatants. The resultant purified solutions polypeptides can be concentrated and/or lyophilized into liquids or solids depending on their final uses.

The following experiments explain the present invention in more detail, and the techniques used therein are conventional ones in this field: For example, the techniques are disclosed by J. Sambrook et al. in *"Molecular Cloning, A Laboratory Manual"*, 2nd edition (1989), published by Cold Spring Harbor Laboratory Press, New York, U.S.A., and by Masami MATSUMURA in *"Laboratory Manual for Genetic Engineering"*(1988), published by Maruzen Co., Ltd., Tokyo, Japan.

EXPERIMENT 1

Expression of Wild-type DNA

Experiment 1-1

Expression of Guinea Pig Wild-type DNA

Experiment 1-1(a)

Preparation of Guinea Pig Wild-type DNA

A guinea pig wild-type DNA encoding L-asparaginase was prepared by the method disclosed in Japanese Patent Kokai No.214,885/96 by the same applicant of this invention. The DNA had the nucleotide sequence of SEQ ID NO:15. A DNA having a polypeptide-encoding region in SEQ ID NO:15, i.e., a sequence of containing the nucleotides 20–1,714 in SEQ ID NO:15, is called "GPA/WT DNA" hereinafter, and the expression product thereof with the amino acid sequence of SEQ ID NO:17 is called "guinea pig wild-type L-asparaginase". SEQ ID NO:17 shows in parallel the nucleotide sequence of GPA/WT DNA and the amino acid sequence (SEQ ID NO:49), encoded thereby.

Experiment 1-1(b)

Preparation of Recombinant DNA

Ten μl of 10×PCR buffer, one μl of 25 mM dNTP mix, one ng of the guinea pig wild-type DNA, obtained in Experiment 1-1(a), as a template were placed in 0.5 ml reaction tube. The mixture was mixed with, as a sense- and anti-sense-primers, an adequate amount of an oligonucleotide chemically synthesized based on the amino acid sequences near the N- and C- termini of SEQ ID NO:15, volumed up with sterilized distilled water to give a total volume of 99.5 μl, and mixed with 0.5 μl of 2.5 units/μl of AmpliTaq DNA polymerase. The nucleotide sequence of the sense primer was 51'-AATCTCGAGCCACCATGGCGCGCGCATCA-3' (SEQ ID NO:19), a nucleotide sequence obtained by adding a common nucleotide sequence in animal cells, as shown by M. Kozak in "*Nucleic Acid Research*", Vol.15, pp.8,125–8, 148 (1987), to the upstream of a region which encodes the N-terminal amino acid sequence of SEQ ID NO:15 and then adding to the further upstream a cleavage site by a restriction enzyme, Xho I. The nucleotide sequence of the anti-sense primer was 5'-CTGCGGCCGCTTATCAGATGGCAGGCGGCAC-3' (SEQ ID NO:20), as a complement to a nucleotide sequence obtained by adding two termination codons to the downstream of a region which encodes the C-terminus of the amino acid sequence of SEQ ID NO:15 and adding a cleavage site by a restriction enzyme, Not I, to the further downstream. The resulting mixture was successively incubated at 94° C. for one min, at 55° C. for one min, and at 72° C. for 3 min, and the series of incubation was repeated 40-times for PCR to amplify DNA. Thus, a DNA containing GPA/WT DNA was obtained and then cleaved by restriction enzymes of Xho I and Not I to obtain an about 1.7 kbp DNA fragment. Twenty-five ng of the DNA fragment was weighed and mixed with 10 ng of a plasmid vector, "pCDM8", commercialized by Invitrogen Corporation, San Diego, U.S.A., which had been cleaved by restriction enzymes of Xho I and Not I. To the DNA mixture thus obtained was added an equal volume of the solution I in "LIGATION KIT VERSION 2" commercialized by Takara Shuzo, Tokyo, Japan, and incubated at 16° C. for 2 hours to obtain a replicable recombinant DNA, "pCGPA/WT".

The recombinant DNA pCGPA/WT was introduced into an *Escherichia coli* MC1061/P3 strain, commercialized by Invitrogen Corporation, San Diego, U.S.A., by competent cell method. The transformant thus obtained was inoculated into L broth medium (pH 7.2) containing 20 μg/ml ampicillin and 10 μg/ml tetracycline followed by cultivation at 37° C. for 18 hours under shaking conditions. The transformants were collected from the culture by centrifugation and subjected to conventional alkali-SDS method to extract the recombinant DNA pCGPA/WT. The analysis of the pCGPA/WT by an automatic sequencer equipped with a fluorophotometer confirmed that it contained GPA/WT DNA, which termination codons were ligated to the 3'-terminus and was ligated to the downstream of a CMV promotor from the 5'- to 3'-termini.

The system using COS-1 (ATCC CRL-1650) as a host, which is a cell line derived from a monkey kidney, was used to express the DNA in the following Experiments 1 and 2. Since the system is for a transient expression, it has a disadvantage that DNAs introduced into transformants could not be stable over several days, and the transformants do not produce the desired polypeptides repeatedly. However, it is known that the number of copies of the desired DNA per cell temporally increases to $10^5$ when plasmid vectors having a replication origin derived from SV40 virus, such as the above mentioned pCDM8, are introduced into the COS-1 cells. With this point of view, the system has a merit that it quite easily analyzes the desired DNA-expression product.

Experiment 1-1(c)

Recombinant DNA Expression in COS-1 Cell

In accordance with the DEAE-dextran method reported by Frederick M. Ausubel et al. in "*Current Protocols in Molecular Biology*" (1987), chapters 9.2.1–9.2.3 and 9.2.5–9.2.6, published by John Wiley and Sons Inc., New York, U.S.A., the recombinant DNA pCGPA/WT in Experiment1-1(b) was introduced into COS-1 cells for its expression. To each well of "3046", a plastic multiwell plate, with 6 wells of 3. 5 cm diameter, commercialized by Becton Dickinson Labware, New Jersey, U.S.A., was added 2.5 ml of DME medium, containing 10 v/v % bovine fetal serum and $1.8 \times 10^5$ COS-1 cells. The cells were cultured at 37° C. in a 5 v/v % $CO_2$ incubator overnight. After removing the culture supernatant by an aspirator and washing the remaining cells with DME medium containing 50 mM Tris-HCI buffer (pH 7.4), each well was charged with 2.5 ml of DME medium containing 2.8 μg/ml PCGPA/WT, 50 Mm Tris-HCl (pH 7.4), 0.4 mg/ml DEAE-dextran and 0.1 mM chloroquine, and incubated at 37° C. for 4 hours in a 5 v/v $CO_2$ incubator. Thereafter, the culture supernatant was removed, and the remaining cells in each well were received with 2.5 ml of 10 mM phosphate buffered saline (hereinafter abbreviated as "PBS") containing 10 v/v % DMSO before incubating at ambient temperature for 2 minutes. After removing the supernatant and washing the remaining cells with DME medium containing 50 mM Tris-HCl (pH 7.4), each well was charged with 2.5 ml of "COS MEDIUM", commercialized by COSMO BIO CO. LTD., Tokyo, Japan, followed by cultivation at 37° C. for 3 days in a 5 v/v % $CO_2$ incubator to express the desired DNA. As a control, the same experiment was carried out using a plasmid vector, pCDM8.

After 3 days' cultivation, the multiwell plates with the cultures were subjected thrice to a treatment of freezing at −80° C. and thawing at ambient temperature to disrupt the cells. The whole cultures were transferred to centrifugal tubes and centrifuged to remove insoluble component s after precipitated, followed by obtaining total soluble fractions, concentrating the fractions using membranes, and adjusting the volume of the total soluble fraction per well to give 0.5 ml for the following analyses.

Experiment 1-1(d)

Assay for L-asparaginase Activity

L-Asparaginase activity was expressed by the unit assayed as follows: Samples were placed in 1.5 ml-reaction tubes in 50 μl each and admixed with 200 μl of 50 mM phosphate buffer (pH 7.0) containing 1.4 mg/ml L-asparagine. After standing at 37° C. for 0, 1, 2, 4, 6 and 16 hours, L-aspartic acid in the reaction mixtures was quantified by an amino acid analyzer. In parallel, 1.0, 0.5 and 0.25 unit/ml dilutions of an L-asparaginase from *Escherichia coli* were provided and quantified for L-aspartic acid after incubating at 37° C. for 0 and one hour, and based on the increased amount of L-aspartic acid, a calibration curve was drawn. By plotting on the calibration curve the increased amounts of L-aspartic acid of the samples, the samples' L-asparaginase activities were estimated. The activity of samples with a lower activity was estimated based on that assayed after 2 hours or more incubation. One unit activity of L-asparaginase was defined as the amount that releases one μmol of ammonia from L-asparagine per minute under the above conditions.

The total soluble fractions obtained in Experiment 1-1(c) were treated similarly as above, and expressed their activities as total L-asparaginase activities that were detected in the soluble fractions from $1.8 \times 10^5$ COS-1 cells. As a result, the activity of the total soluble fraction in Experiment 1-1(c) was 0.083 unit, and the control gave no activity.

Experiment 1-1(e)

Western Blotting

An anti-L-asparaginase antibody was prepared as follows: An oligopeptide of a sequence Gly-Ser-Gly-Asn-Gly-Pro-Thr-Lys-Pro-Asp-Leu-Leu-Gln-Glu-Leu-Arg-Cys (SEQ ID NO:21), was synthesized chemically in a usual manner. Keyhole Limped Hemocyanin was linked to the C-terminus of the oligopeptide. The resultant was purified and used to immunize rabbits in a usual manner. The rabbits were immunized 6 times 2 weeks about, then the whole blood was collected and subjected to salting out with 50 w/v % ammonium sulfate to obtain an anti-L-asparaginase antiserum.

In accordance with the method reported by U. K. Laemli et al. in "*Nature*", Vol. 227, pp. 680–685 (1970), 0.2 ml of the total soluble fraction in Experiment 1-1(c) was subjected to 12.5 w/v % SDS-polyacrylamide gel electrophoresis (hereinafter abbreviated as "SDS-PAGE"). The polypeptides migrated were transferred to a nitrocellulose membrane and subjected to Western blotting using the above anti-L-asparaginase anti-serum, in accordance with the method reported by H. Towbin in "*Proceedings of the National Academy of Sciences of the U.S.A.*", Vol.76, pp.4,350–4,354 (1979). For color development, alkaline phosphatase system was used. Comparing with the control and molecular weight markers, both the identification of bands specifically stained in the sample and the measurement of the molecular weight of each subunit of the L-asparaginase were carried out. The molecular weight markers used were bovine serum albumin (67 kDa), ovalbumin (45 kDa), soy bean trypsin inhibitor (20.1 kDa) and α-lactalbumin (14.4 kDa), and stained with amide black. The total soluble fraction in Experiment 1-1(c) gave no clear band.

Experiment 1-1(f)

Measurement of Molecular Weight on Gel Filtration

Two ml of the total soluble fraction in Experiment 1-1(c) was subjected to gel filtration column chromatography using "HILOAD SUPERDEX 200 COLUMN", with an inner diameter of 16 mm and a length of 60 cm, commercialized by Pharmacia LKB Biotechnology AB, Uppsala, Sweden, equilibrated with PBS. Based on the L-asparaginase activity of the eluted fractions, the molecular weight of the guinea pig wild-type L-asparaginase in a native form was examined. The molecular weight markers used were thyroglobulin (699 kDa), ferritin (440 kDa), catalase (232 kDa), aldolase (158 kDa), bovine serum albumin (67 kDa) and ovalbumin (43 kDa). The peak of L-asparaginase activity in the eluted fractions was observed in a position corresponding to a molecular weight of about 300 kDa.

Since no clear band was detected by Western blotting, the molecular weight of the wild-type L-asparaginase in a dissociated form could not be detected, while the molecular weight in a native form was estimated to be about 300 kDa based on the result of gel filtration. The molecular weights of L-asparaginase in a native and dissociated form, purified from guinea pig L-asparaginase in serum, were respectively estimated to be about 190 kDa on gel filtration and about 43 kDa on SDS-PAGE. As disclosed in Japanese Patent Kokai No.214,885/96 by the same applicant of the present invention, 3 partial amino acid sequences of a guinea pig L-asparaginase in serum were observed in a region of amino acids 10–236 in the sequence of guinea pig wild-type L-asparaginase. While, two consensus amino acid sequences essential for the expression of L-asparaginase activity, i.e., SEQ ID NOs:1 and 2, as proposed by E. Harms in "*FEBS letters*", Vol. 285, pp.55–58 (1991) based on the results of experiments on L-asparaginase derived from *Escherichia coli*, correspond to the sequences of amino acids 16–19 and 114–118 in the amino acid sequence of the guinea pig wild-type L-asparaginase. In view of these and the results in Experiment 1-1, the present inventors estimated that the guinea pig wild-type L-asparaginase may require a region of amino acids about 1–400 in the amino acid sequence to express the activity. In Experiment 2-1, to examine the L-asparaginase activities of C-terminal defective mutants as homologues of the guinea pig wild-type L-asparaginase, the expression products of DNA homologues from a guinea pig were tested for properties and features.

Experiment 1-2

Expression of Human Wild-type DNA

A human wild-type DNA encoding L-asparaginase was prepared according to the method in Japanese Patent Kokai No.214,855/96 by the same applicant of the present invention. The DNA had the nucleotide sequence of SEQ ID NO:16. Hereinafter, a DNA having a polypeptide-encoding region in SEQ ID NO:16, i.e., a sequence of nucleotides 93–1,811 in SEQ ID NO:16, was named "HA/WT DNA", and a polypeptide, as the expression product of HA/WT DNA, having the amino acid sequence of SEQ ID NO:18, which is "human wild-type L-asparaginase". SEQ ID NO:18 shows the nucleotide sequence of GPA/WT DNA and the amino acid sequence (SEQ ID NO:50), encoded thereby.

Except for the template and the sense- and anti-sense-primers, PCR was performed under the same conditions as used in Experiment 1-1(b). As a template, the human wild-type DNA in Experiment 1-2 was used. As a sense- and anti-sense-primers, oligonucleotides with sequences of 5'-AATCTCGAGCCACCATGGCGCGCGCG GTG-3' (SEQ ID NO:22), and 5'-CTGCGGCCGCTTATCAGACACCAGGCAGCAC-3' (SEQ ID NO:23), were respectively used. The DNA thus amplified was continuously treated with the same method as used in Experiment 1-1(b) to prepare a recombinant DNA, "pCHA/WT". After sequencing, the pCHA/WT was introduced into COS-1 cells and expressed followed by analyzing the expression product similarly as in Experiment 1-1.

In contrast to the guinea pig wild-type L-asparaginase, the experiment system could not detect the human wild-type L-asparaginase activity. It was presumably due to that the human wild-type L-asparaginase had a lower specific activity than that of the guinea pig wild-type one, and this forced to examine the properties of expression products by DNA homologues from human in Experiment 2-2.

EXPERIMENT 2

Expression of DNA Homologue

Experiment 2-1

Expression of DNA Homologue Originating from Guinea Pig

A termination codon was replaced for the nucleotide sequence in a specific position of the guinea pig wild-type DNA to obtain a DNA homologue: A DNA was obtained by PCR method by replacing a termination codon for a codon of the nucleotides 1,090–1,092 or 1,012–1,014 in SEQ ID NO:17. Except for the nucleotide sequence of anti-sense primer, PCR was performed under the same conditions as used in Experiment 1-1(b). As an anti-sense primer, an oligonucleotide with a sequence of 5'-CTGCGGCCGCTTATCATGCCGTGGGCAGTGT-3' (SEQ ID NO:24), or 5'-CTGCGGCCGCTTATCAGCCCAACACGTAGGA-3' (SEQ ID NO:25), was used to prepare the two-types of DNAs. The amplified DNAs were treated similarly as in Experiment1-1(b) to obtain recombinant DNAs, "pCGPA/D364stp" and "pCGPA/L338stp". By sequencing similarly, it was confirmed that pCGPA/D364stp and pCGPA/L338stp had DNAs, encoding the sequences of amino acids 1–363 and 1–337 in the guinea pig wild-type L-asparaginase, respectively, and had a termination codon at their 3'-termini free of intervening sequences. Hereinafter, the polypeptide-encoding regions of the DNAs are respectively named "GPA/D364stp DNA" and "GPA/L338stp DNA". GPA/D364stp DNA and "PA/L338stp DNA" were ligated in the downstream of a CMV promoter in the direction from the 5'- to 3'-termini. The DNAs expression products may be named "guinea pig L-asparaginase homologues".

The above recombinant DNAs were introduced into COS-1 cells and examined similarly as in Experiment 1-1. As controls, pCGPA/WT and pCDM8 in Experiment 1-1(b) were similarly treated and examined. Table 1 shows the results.

TABLE 1

| Recombinant DNA | L-asparaginase activity (unit) | Molecular weight (kDa) *1 | Molecular weight (kDa) *2 |
|---|---|---|---|
| pCGPA/WT | 0.083 | — | about 300 |
| pCGPA/D364stp | 0.228 | about 40 | about 140 |
| pCGPA/L338stp | N.D. *3 | about 40 | — |
| pCDM8 | N.D. *3 | — | — |

Note: The symbols "*1", "*2" and "*3" mean that the value was determined by Western blotting, the value was determined by gel filtration, and the activity was not detected, respectively.

As shown in Table 1, the activities of the expression products of GPA/WT DNA and GPA/D364stp DNA were detected, but not for GPA/L338stp DNA. These results suggest that a region of amino acids 1–363 in the guinea pig wild-type L-asparaginase may be enough for sufficiently expressing the L-asparaginase activity. This amino acid sequence, amino acids 1–363 in the guinia pig wild-type, is SEQ ID NO:4, and a nucleotide sequence which encodes the amino acid sequence is SEQ ID NO:10. The amino acid sequence of the guinea pig wild-type L-asparaginase is SEQ ID NO:5.

Experiment 2-2

Expression of DNA Homologue Originating From Human

DNA homologues were prepared by replacing specific codons in the human wild-type DNA with termination codons or codons for different amino acids: The DNA homologues were prepared by replacing termination codons for the nucleotides 1096–1098 in SEQ ID NO:18 by applying PCR method. Except for the template and the sense- and anti-sense-primers, PCR was performed under the same conditions as used in Experiment 1-1(b). As a template, the human wild-type DNA in Experiment 1-2 was used. As a sense- and anti-sense-primers, the oligonucleotides with sequences of 5'-AATCTCGAGCCACCATGGCGCGCGCGGTG-3' (SEQ ID NO:22), and 5'-CTGCGGCCGCTCATTACACCGAGGGTGGCGT-3' (SEQ ID NO:26), were respectively used. The amplified DNA was treated similarly as in Experiment 1-1 to obtain a recombinant DNA, "pCHA/E366stp", and sequenced. It was confirmed that pCHA/E366stp contained a DNA encoding amino acids 1–365 in SEQ ID NO:16 and a termination codon at the 3'-terminus free of intervening sequences The polypeptide-encoding region was named "HA/E366stp DNA", hereinafter. HA/E366stp DNA was ligated to the downstream of a CMV promotor in the direction from the 5'- to 3'-termini.

To change specific codons in DNAs into ones for different amino acids, the over lap extension method reported by Robert M. Horton et al. in "*Methods in Enzymology*", Vol. 217, pp. 270–279 (1993), published by Academic Press, Inc., San Diego, U.S.A., was used. The method is summarized in FIG. 1 and explained as follows: First, mutagenic primers A and B, where the nucleotides to be mutagenized were substituted by desired different ones complementary to one another, were prepared. The mutagenic primer A was a sense strand, and the mutagenic primer B was an anti-sense strand. A set of 5'- and 3'-terminal primers, which amplify the whole region of the desired DNA, were prepared, and they were respectively a sense- and anti-sense-strands. Second, conventional PCR was performed using the 5'-terminal primer, the mutagenic primer A, and as a template, a DNA with the original nucleotide sequence. In parallel, another PCR as was performed using the same DNA as a template, the 3'-terminal primer, and the mutagenic primer B. These two PCRs were named "first step PCRs". Third, two DNAs amplified in the first step PCRs were mixed with the 5'- and 3'-terminal primers as used in the first step PCRs followed by performing PCR as a second step PCR. The two DNA fragments amplified in the first step PCRs were used as primers and templates to generate mutagenized DNAs, while the 5'- and 3'-terminal primers were used as primers to amplify the mutagenized DNAs. By this method, DNAs into which were introduced 7 types nucleotide substituents, i.e., 7 DNA homologues were prepared. The 7 types nucleotide substituents and consequent changes of the encoded amino acid sequences are summarized in Table 2. The template DNA and mutagenic primers A and B used to prepare the 7 DNA homologues were summarized in Table 3. The 5'- and 3'-terminal primers were respectively equal to the sense- and anti-sense-primers as used to prepare pCHA/E366stp in Experiment 2-2.

TABLE 2

| DNA homologue | Recombinant DNA | Nucleotide substitution (upper line) and consequential change of amino acid (lower line)* |
|---|---|---|
| HA/MUT1 DNA | pCHA/MUT1 | C894G, A902G, G952A, G953A and G1096T |
| | | H298Q, Q301R, G318N and E366stp |
| HA/MUT2 DNA | pCHA/MUT2 | C894G, A902G and G1096T |
| | | H298Q, Q301R and E366stp |
| HA/MUT3 DNA | pCHA/MUT3 | C894G, G952A, G953A and G1096T |
| | | H298Q, G318N and E366stp |
| HA/MUT4 DNA | pCHA/MUT4 | A902G, G952A, G953A and G1096T |
| | | Q301R, G318N and E366stp |
| HA/MUT5 DNA | pCHA/MUT5 | C894G and G1096T |
| | | H298Q and E366stp |
| HA/MUT6 DNA | pCHA/MUT6 | A902G and G1096T |
| | | Q301R and E366stp |

TABLE 2-continued

| DNA homologue | Recombinant DNA | Nucleotide substitution (upper line) and consequential change of amino acid (lower line)* |
|---|---|---|
| HA/MUT7 DNA | PCHA/MUT7 | G952A, G953A and G1096T<br>G318N and E366stp |

*Numbers in the upper lines in each column mean a nucleotide number in SEQ ID NO: 18.
Numbers in the lower lines in each column means an amino acid residue number in SEQ ID NO: 18.
Alphabets on the left and right of the numbers in the upper lines show nucleotides before and after the nucleotide substitution, respectively.
Alphabets on the left and right of the numbers in the lower lines show amino acids before and after the nucleotide substitution, respectively.
The symbol "stp" means that a termination condon was substituted for a codon in the wild-type DNA.
Names for the 7 DNA homologues and the recombinant DNAs containing the DNA homologues are shown in parallel.

TABLE 3

| DNA homologue | Template DNA | Nucleotide sequences of mutagenic primers A (upper line) and B (lower line)* |
|---|---|---|
| HA/MUT1 DNA | pCHA/MUT7 | the same as used for HA/MUT2 DNA preparation<br>the same as used for HA/MUT2 DNA preparation |
| HA/MUT2 DNA | pCHA/E366stp | 5'-CCCCcGGAGGCAcTGGGT-3'(SEQ ID NO:27)<br>5'-ACCCAgTGCCTCCgGGGG-3'(SEQ ID NO:28) |
| HA/MUT3 DNA | pCHA/MUT7 | the same as used for HA/MUT5 DNA preparation<br>the same as used for HA/MUT5 DNA preparation |
| HA/MUT4 DNA | pCHA/MUT7 | the same as used for HA/MUT6 DNA preparation<br>the same as used for HA/MUT6 DNA preparation |
| HA/MUT5 DNA | pCHA/E366stp | 5'-CCCCTGGAGGCAcTGGGT-3'(SEQ ID NO:29)<br>5'-ACCCAgTGCCTCCAGGGG-3'(SEQ ID NO:30) |
| HA/MUT6 DNA | pCHA/E366stp | 5'-CCCCcGGAGGCAGTGGGT-3'(SEQ ID NO:31)<br>5'-ACCCACTGCCTCCgGGGG-3'(SEQ ID NO:32) |
| HA/MUT7 DNA | pCHA/E366stp | 5'-GACGttGGCTCCCGCCAT-3'(SEQ ID NO:33)<br>5'-ATGGCGGGAGCCaaCGTC-3'(SEQ ID NO:34) |

Note: Small letters mean nucleotides which were substituted for those in human wild-type DNA.

The obtained DNA homologues from human were treated similarly as in Experiment 1-1 to obtain recombinant DNAs "pCHA/MUT1", "pCHA/MUT2", "pCHA/MUT3", "pCHA/MUT4", "pCHA/MUT5", "pCHA/MUT6" and "pCHA/MUT7". The expression products of the DNA homologues, obtained in Experiment 2-2, may be named "human L-asparaginase homologues", hereinafter. After sequencing, these DNA homologues were introduced into COS-1 cells, followed by expression and assay. As controls, pCHA/WT obtained in Experiment 1-2 and pCDM8 were treated and examined. Signal intensities of bands, detected by Western blotting, were evaluated by densitometry to compare quantitatively the expressed products. The results were in Table 4.

TABLE 4

| Recombinant DNA | L-asparaginase activity (unit) *1 | Molecular weight (kDa) *2 | Quantity *3 | Molecular weight (kDa) *4 |
|---|---|---|---|---|
| pCHA/WT | N.D. | — | — | — |
| pCHA/E366stp | N.D. | about 40 | 2.3 | — |
| pCHA/MUT1 | 0.021 | about 40 | 0.4 | about 140 |
| pCHA/MUT2 | 0.031 | about 40 | 0.9 | about 140 |
| pCHA/MUT3 | 0.009 | about 40 | 0.1 | about 140 |
| pCHA/MUT4 | N.D. | about 40 | 0.2 | — |
| pCHA/MUT5 | 0.006 | about 40 | 1.2 | about 140 |
| pCHA/MUT6 | N.D. | about 40 | 1.9 | — |
| pCHA/MUT7 | N.D. | about 40 | 0.2 | — |
| pCDM8 | N.D. | — | — | — |

Note: The symbols "*1", "*2", "*3" and "*4" mean the activity was not detected, the value was determined by Western blotting, the value indicates the signal intensity of the band detected on Western blotting and quantified by densitometry, and the value was determined by gel filtration, respectively.

The results in Table 4 indicate that human L-asparaginases both in the wild-type and in the C-terminal defected mutant, i.e., the expression product of HA/E366stp DNA, as the one of the homologues, had a lower specific activity than that from guinea pigs. In addition, these results indicate that the specific activity of L-asparaginases among those of point mutants, which some of the amino acids inherent to the human wild-type L-asparaginase were substituted by different ones, increased to a detectable level. The human DNA homologues such as HA/MUT1, HA/MUT2, HA/MUT3 and HA/MUT5, which the expression products gave a detectable level of activity, have SEQ ID NOs:11 to 14, respectively, and encoding SEQ ID NOs:6 to 9, respectively.

Based on the results in the above experiments, the present inventors found that polypeptides from mammal may require the amino acid sequence of SEQ ID NO:3 (where the symbol "Xaa" meant "glutamine" or "arginine") to express a detectable level of L-asparaginase activity in the expression and assay systems in Experiments 1 and 2, in addition to conventionally known as such amino acid sequences of SEQ ID NOs:1 and 2. The animo acid sequence of the guinea pig wild-type L-asparaginase contains the SEQ ID NO:3 in the region the amino acids 298–302. Examples of such polypeptides, having all the amino acid sequences of SEQ ID NOs:1 to 3, include those having SEQ ID NOs:4 and 5 from guinea pigs and those having SEQ ID NOs:6 to 9 from human.

Based on the above findings, the present inventors invented the polypeptides having L-asparaginase activity. The following examples explain the present invention, and the techniques used therein are conventional ones used in the art, and of course, they are not restrictive to the present invention:

EXAMPLE A-1

Polypentides Having L-asparaginase Activity

Example A-1(a)

Preparation of Transformant

Ten $\mu$l of 10×PCR buffer, one $\mu$l of 25 mM dNTP mix, one ng of the recombinant DNA pCGPA/WT DNA obtained in Experiment 1-1 as a template, and an adequate amount of oligonucleotides as a sense- and anti-sense-primers synthesized chemically based on the 5'- and 3'-terminal sequences of GPA/WT DNA were placed in 0.5 ml reaction tube. The mixture was mixed with sterilized distilled water to give a total volume of 99.5 $\mu$l, and 0.5 $\mu$l of 2.5 units/$\mu$l AmpliTaq DNA polymerase were further added. The sequence of the sense primer was 5'-GCGAATTCATGGCGCGCGCATCA-3' (SEQ ID NO:35), which was a nucleotide sequence obtained by adding a cleavage site by a restriction enzyme, Eco RI, to the upstream of the 5'-terminus of GPA/WT DNA. The sequence of the anti-sense primer was 5'-GCAAGCTTTCAGATGGCAGGCGGCAC-3' (SEQ ID NO:36), which was complementary to a nucleotide sequence prepared by adding a termination codon to the 3'-terminus of GPA/WT DNA and then adding a cleavage site by a restriction enzyme, Hin dIII, to the downstream. The above mixture was subjected to 40 cycles of successive incubations at 94° C. for one min, at 55° C. for one min, and 72° C. for 3 min to perform PCR. By cleaving the amplified DNA by restriction enzymes Eco RI and Hin dIII, a Eco RI-Hin dIII fragment with a length of about 1.7 kbp was obtained. Twenty-five ng of the DNA was mixed with 10 ng of plasmid vector "pKK223-3", commercialized by Pharmacia LKB Biotechnology AB, Uppsala, Sweden, which had been cleaved by restriction enzymes Eco RI and Hin dIII, and then mixed with the solution I in "LIGATION KIT VERSION 2" commercialized by Takara Shuzo Inc., Tokyo, Japan, in an equal volume of the DNA mixture, followed by incubation at 16° C. for 2 hours to obtain a replicable recombinant DNA, "pKGPA/WT".

The recombinant DNA pKGPA/WT was introduced into an *Escherichia coli* strain "JM105" by the competent cell method. The resulting transformant "J-GPA/WT" was inoculated to L broth medium (pH 7.2) containing 50 $\mu$g/ml ampicillin and cultured at 37° C. for 18 hours under shaking conditions. The transformants collected by centrifugation from the culture were subjected to a conventional alkali-SDS method to extract the recombinant DNA pKGPA/WT. As shown in FIG. 2, analysis using an automatic sequencer equipped with a fluorophotometer revealed that GPA/WT DNA of SEQ ID NO:17 ligated to the downstream of a Tac promotor in the direction from the 5'- to 3'-termini. In addition, it was confirmed that a termination codon was ligated to the downstream of GPA/WT DNA without intervening sequences.

Example A-1(b)

Production of Polypeptide

The transformant J-GPA/WT was inoculated into L broth medium (pH 7.2), containing 50 $\mu$g/ml ampicillin, and cultured at 37° C. for 18 hours under shaking conditions to obtain a seed culture. Eighteen L of a fresh preparation of the same medium was placed in a 30-L jar fermenter, inoculated with one v/v % of the seed culture, and cultured at 37° C. under aeration-agitation conditions. A portion of the culture was placed in a cuvette with 1-cm in thickness, incubated until the absorbance at a wavelength of 650 nm reached to about 1.5, admixed with IPTG to give a final concentration of 0.1 mM, and incubated for 5 hours. The cells centrifugally collected from the culture were suspended in a mixture solution (pH 7.2) containing 139 mM NaCl, 7 mM $Na_2HPO_4$ and 3 mM $NaH_2PO_4$, and supersonicated to disrupt the cells, followed by centrifuging the resultant to obtain a supernatant.

Ammonium sulfate was added to the supernatant under ice-chilling conditions to give a concentration of 50 w/v % and then dissolved to homogeneity. After standing for several minutes, the precipitates were collected by centrifugation, dissolved in 20 mM Tris-HCl buffer (pH 8.0), and dialyzed against a fresh preparation of the same buffer followed by applying the dialyzed solution to "Q SEPHAROSE FF COLUMN", commercialized by Pharmacia LKB Biotechnology AB, Uppsala, Sweden, equilibrated with the same buffer. After washing sufficiently with the same buffer, the column was fed with a linear gradient buffer of NaCl increasing from 0 M to 0.5 M in 20 mM Tris-HCl buffer (pH 8.0). The fractions eluted at about 0.1–0.3 M NaCl were collected, and the solvent was replaced with 10 mM sodium-phosphate buffer (pH 7. 5) while concentrating with membranes. The concentrated solution was then applied to "L-ASPARAGINE AGAROSE", commercialized by Sigma Chemical Co., St.

Louis, U.S.A, equilibrated with the same buffer. After washing with the same buffer, 10 mM sodium phosphate buffer (pH 7.5) containing 0.5 M NaCl was fed to the column for elution. The eluted fractions were pooled and concentrated by using a membrane. The concentrate was applied to "HILOAD SUPERDEX 200 COLUMN", commercialized by Pharmacia LKB Biotechnology AB, Uppsala, Sweden, equilibrated with Tris-HCl buffer (pH 8.0) containing 10 v/v % glycerol, and eluted from the column. The eluted fractions, containing substances with a molecular weight of about 300 kDa, were collected to obtain a purified polypeptide with a purity of 90% or more in a yield of about 0.1 mg/ml culture.

Example A-1(c)

Physicochemical Property of Polypeptide

The purified polypeptide in the above was analyzed to determine the physicochemical properties: The molecular weight of the purified polypeptide in a native form was determined by gel filtration similarly as in Experiment 1-1(e). The peak for L-asparaginase activity of the eluted fractions was found at a position corresponding to a molecular weight of about 300 kDa. The molecular weight of the purified polypeptide in a dissociated form was determined by SDS-PAGE as used in Experiment1-1(e). The main band was observed at a position corresponding to a molecular weight of about 50±10 kDa. The results indicate that the purified polypeptide exists in a multimer as a native form. Considering errors in measurement by the above methods and the fact that all the known L-asparaginases from

*Escherichia coli* etc., other than mammal, exist in a tetrameric form, it can be estimated that the purified polypeptide exists in a tetrameric form. The method as used in Experiment 1-1(d) confirmed that the purified polypeptide has an L-asparaginase activity.

Example A-2(a)

Preparation of Transformant

FIG. 3 summarizes the procedures to prepare transformants. PCR was performed under the same conditions as used in Example A-1(a) except for the nucleotide sequences of a sense- and anti-sense-primers. As the sense- and anti-sense-primers, oligonucleotides with the nucleotide sequences of 5'-GTGAATTCGGAGGTTCAGATGGCGCGCGCATCA-3' (SEQ ID NO:37), and 5'-CTGCGGCCGCTCAGATGGCAGGCGGCAC-3' (SEQ ID NO:38), were respectively used. The DNA thus amplified was cleaved by restriction enzymes Eco RI and Not I to obtain an about 1.7 kbp Eco RI-Not I fragment. Seventy ng of the DNA fragment was mixed with 50 ng of a plasmid vector, "pBPV", commercialized by Pharmacia LKB Biotechnology AB, Uppsala, Sweden, cleaved in advance by restriction enzymes Xho I and Not I, and 25 ng of each of 4 oligonucleotides as linkers with nucleotide sequences of 5'-TCGAGCCACCATGAAGTGTTCGTGGGTTATT-3' (SEQ ID NO:39), 5-TTCTTCCTGATGGCCGTAGTGACAGGAG-3' (SEQ ID NO:40), 5'-AATTCACTCCTGTCACTACGGCCATCAGGA-3' (SEQ ID NO:41), and 5'-AGAAAATAACCCACGAACACTTCATGGTGGC-3' (SEQ ID NO:42). The oligonucleotides for linkers were synthesized in a usual manner and used after reacted with T4 polynucleotide kinase, commercialized by Pharmacia LKB Biotechnology AB, Uppsala, Sweden, and purified by ethanol-precipitation. To the DNA mixture was added the solution I in "LIGATION KIT VERSION 2", commercialized by Takara Shuzo, Tokyo, Japan. The mixture was incubated at 16° C. for 2 hours to obtain a replicable recombinant DNA "pBIgGPA/WT".

Figure 4:
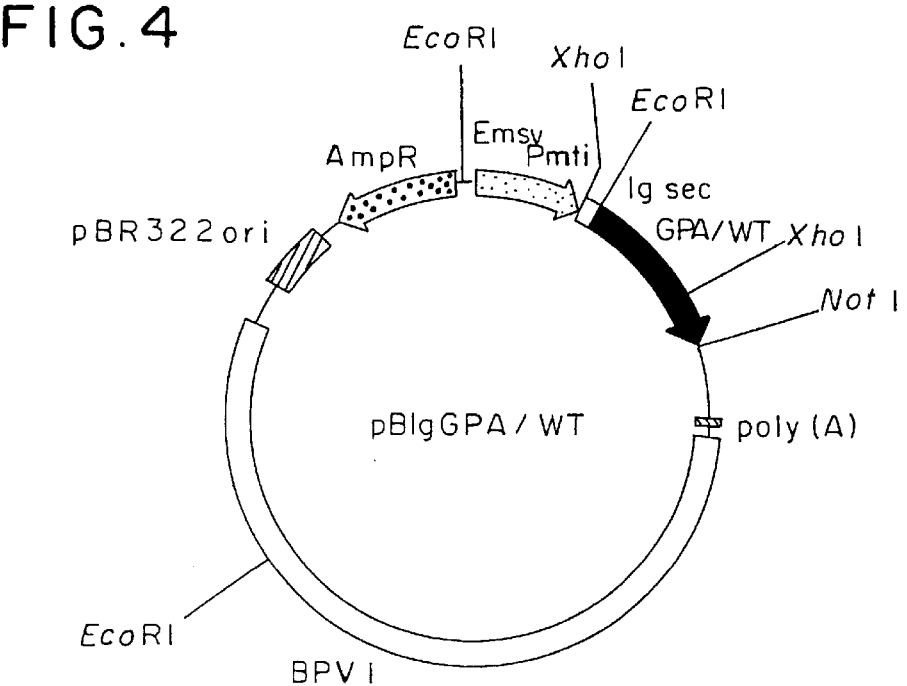
FIG. 4 is a restriction map of recombinant DNA pBIgGPA/WT.
Figure 5:
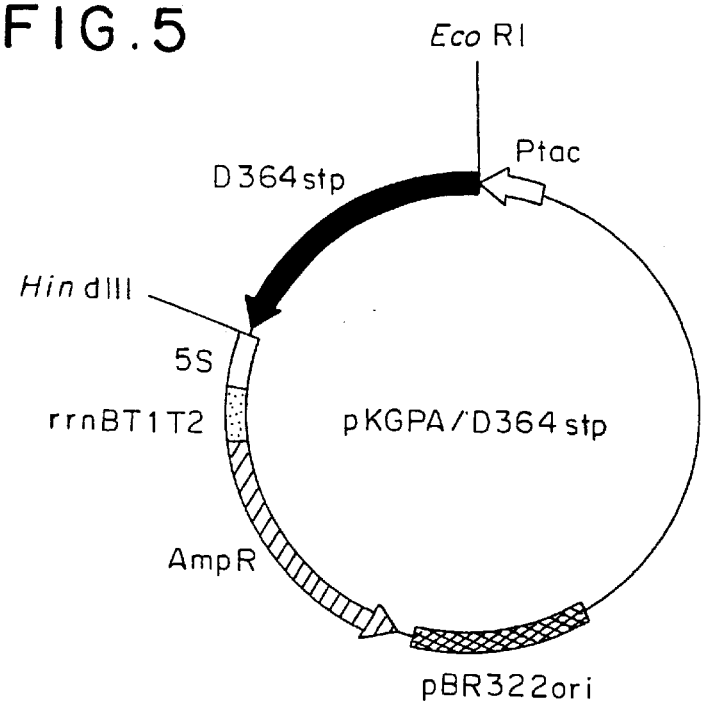
FIG. 5 is a restriction map of recombinant DNA pKGPA/D364stp.
Figure 6:
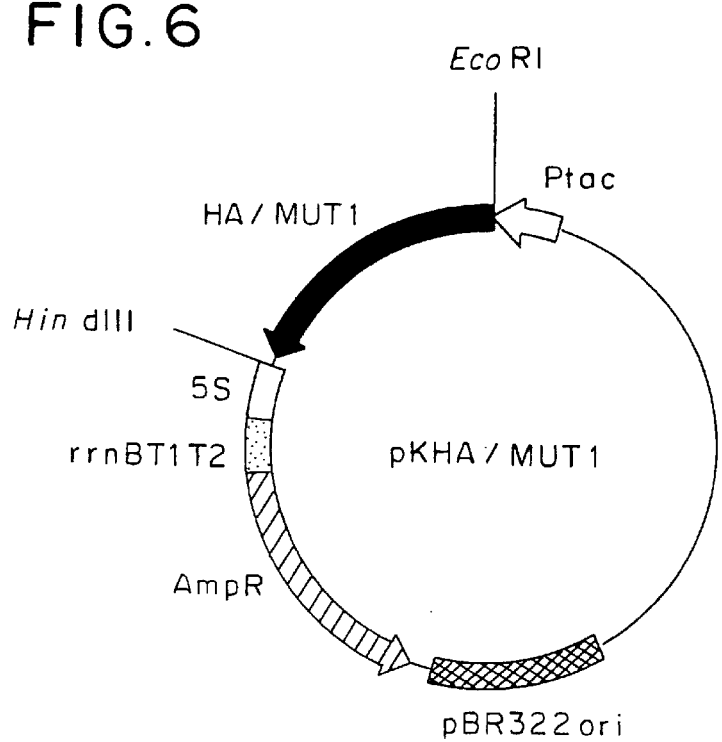
FIG. 6 is a restriction map of recombinant DNA pKHA/MUT1.
Figure 7:
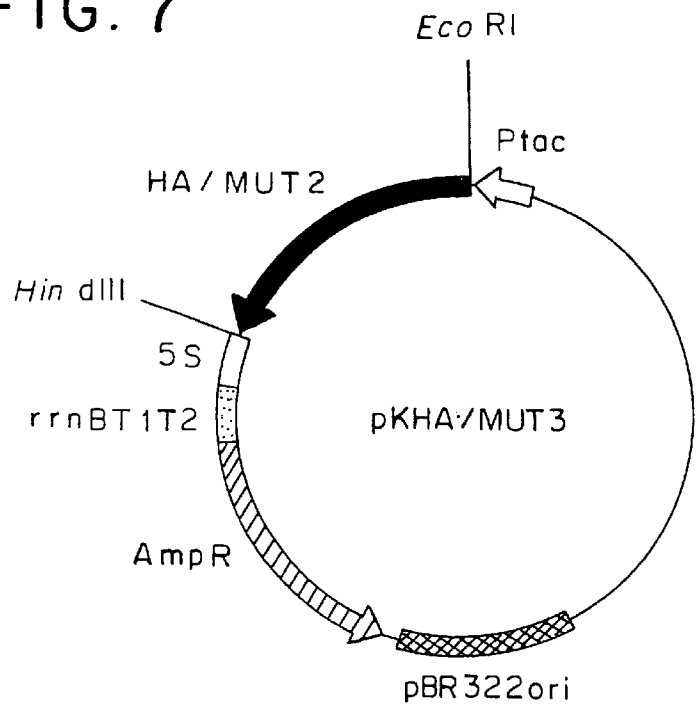
FIG. 7 is a restriction map of recombinant DNA pKHA/MUT2.
Figure 8:
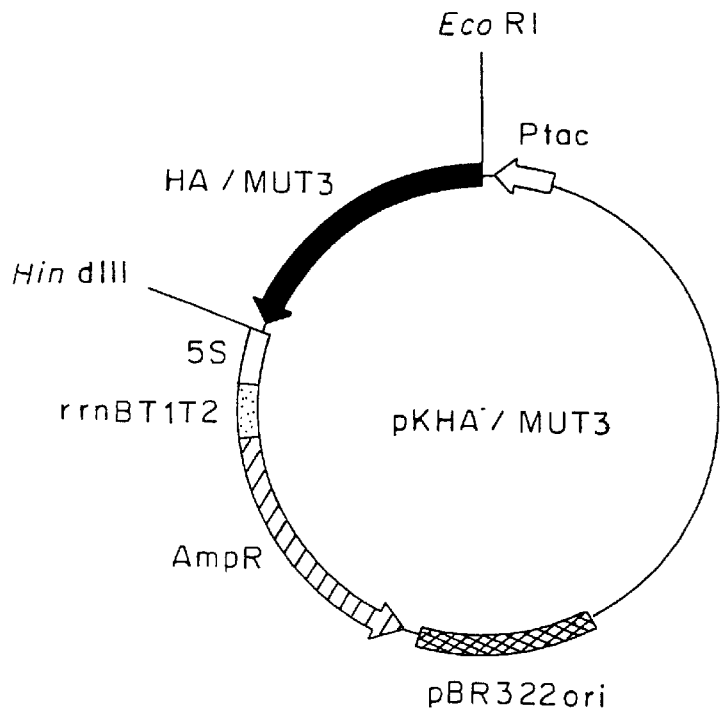
FIG. 8 is a restriction map of recombinant DNA pKHA/MUT3.
Figure 9:
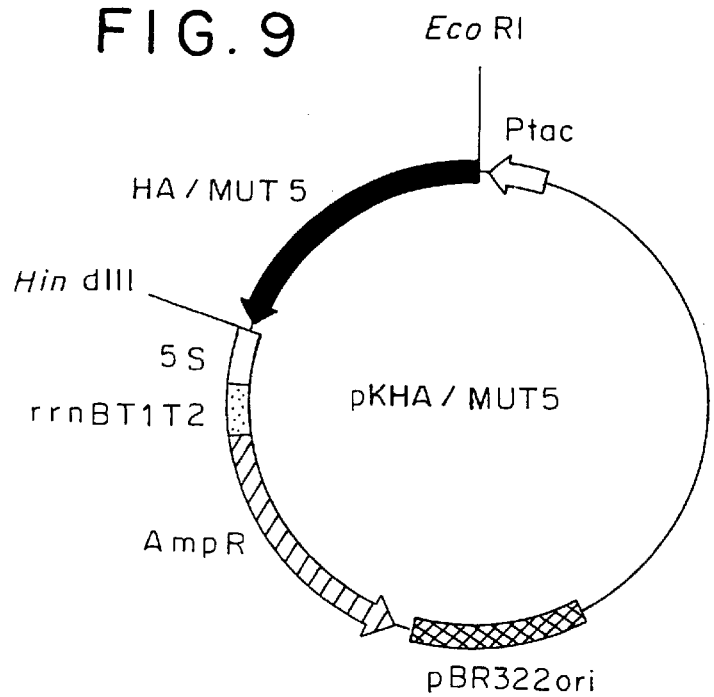
FIG. 9 is a restriction map of recombinant DNA pKHA/MUT5.
Figure 10:
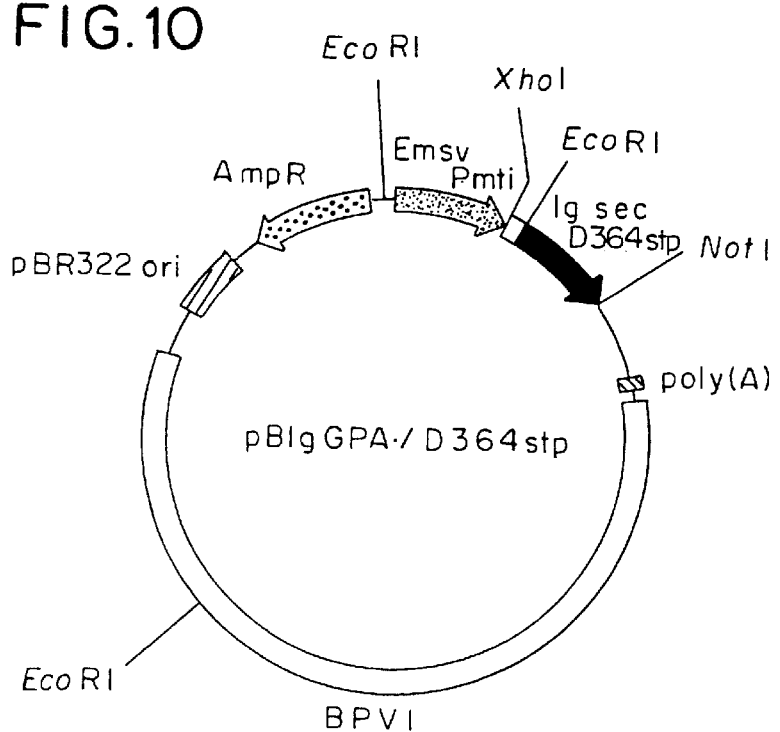
FIG. 10 is a restriction map of recombinant DNA pBIgGPA/D364stp.
Figure 11:
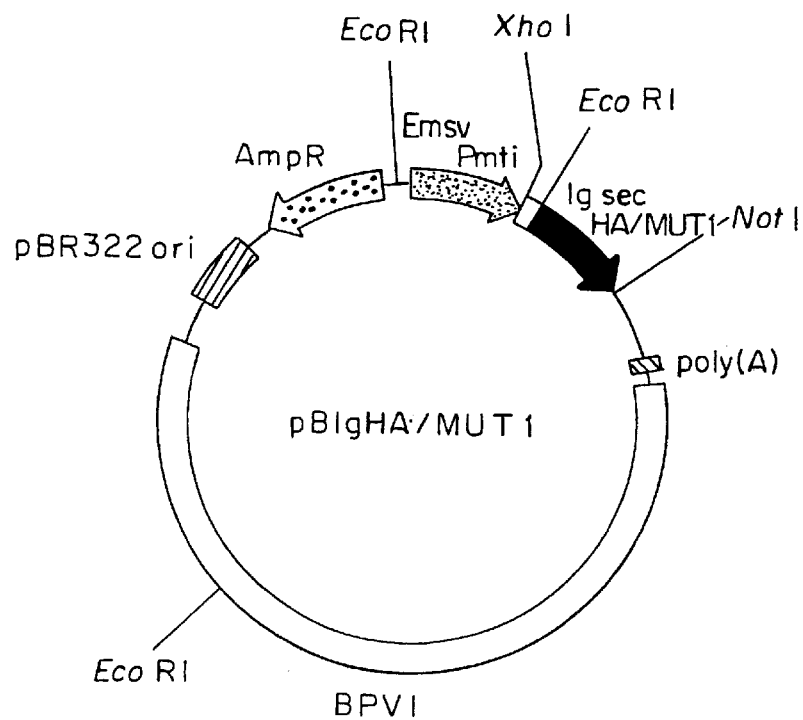
FIG. 11 is a restriction map of recombinant DNA pBIgHA/MUT1.
Figure 12:
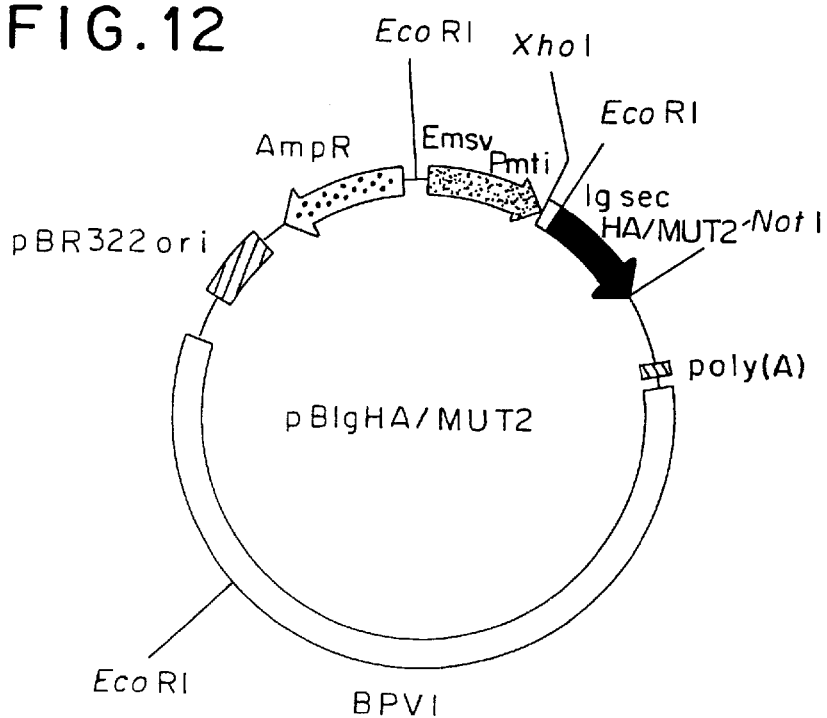
FIG. 12 is a restriction map of recombinant DNA pBIgHA/MUT2.
Figure 13:
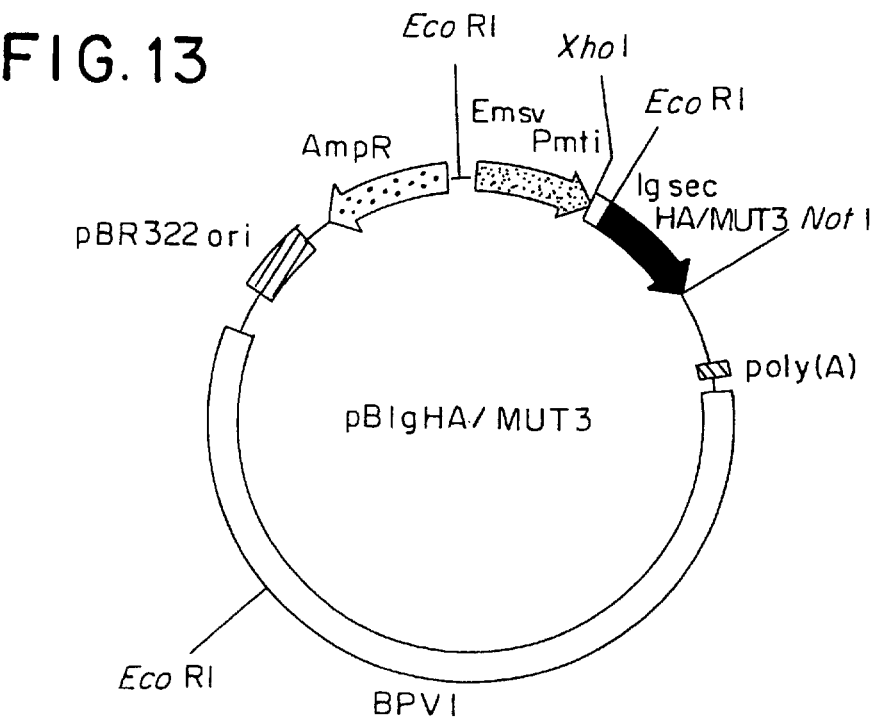
FIG. 13 is a restriction map of recombinant DNA pBIgHA/MUT3.
Figure 14:
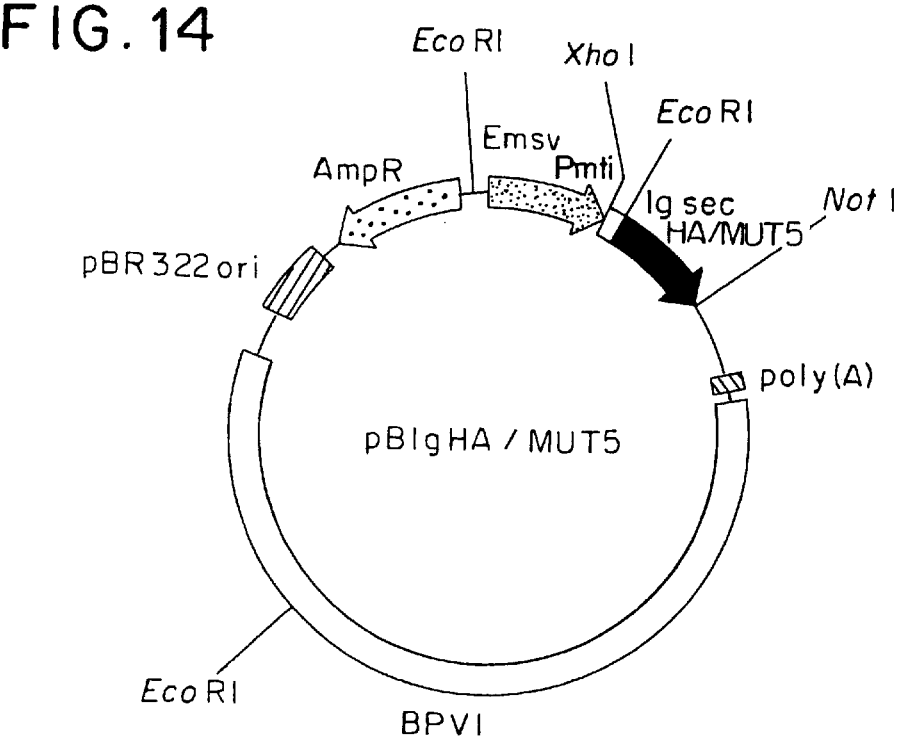
FIG. 14 is a restriction map of recombinant DNA pBIgHA/MUT4.

The recombinant DNA pBIgGPA/WT was introduced into an *Escherichia coil* HB101 strain by the competent cell method. The transformant thus obtained was inoculated into L broth medium (pH 7.2) containing 50 µg/ml ampicillin followed by cultivation at 37° C. for 18 hours under shaking conditions. The transformants, collected by centrifuging the resulting culture, were subjected to a conventional alkali-SDS method to extract the recombinant DNA pBIgGPA/WT. The nucleotide sequence analysis using an automatic sequencer confirmed that the recombinant DNA pBIgGPA/WT had the structure in FIG. 4: A DNA encoding a polypeptide containing a signal sequence for immunoglobulin secretion, as shown by D. F. Stern et al. in *"Science"*, Vol. 235, pp.321–324 (1984), i.e., "Ig sec DNA" was ligated to the downstream of a region for transcriptional regulation, comprising an enhancer derived from long terminal repeats of Moloney Mouse Sarcoma Virus (Emsv), and a promotor derived from Mouse metallothionein I gene (Pmti). Furthermore, GPA/WT DNA was ligated in the same frame to the downstream of the Ig sea DNA in the direction from the 5'- to 3'-termini of GPA/WT DNA. It was also confirmed that a termination codon exists in the 3'-terminus of GPA/WT DNA without intervening sequences.

The recombinant DNA pBIgGPA/WT was introduced into a cell line C127 (ATCC CRL-1616), derived from a mouse, by using a lipofectin® reagent commercialized by Life Technologies, Inc., Gaitherburg, U.S.A, according to the attached protocol. The transformants with the recombinant DNA were selected based on the lack of proliferation-regulatory ability, i.e., focus-forming ability, as a first selection. The cells around those containing foci were collected using sterilized filter papers and subjected to a conventional limiting dilution method to form single cells which were then selected depending on the productivity of L-asparaginase, as final selection. Thus, a transformant, "C-GPA/WT", was obtained.

Example A-2(b)

Production of Polypeptide

The transformant C-GPA/WT was inoculated into a well of "3046", a plastic multiwell plate with 6 wells, 3.5 cm in diameter, commercialized by Becton Dickinson Labware, New Jersey, U.S.A, with DME medium containing 10 v/v % bovine fetal serum, and cultured to be confluent as a seed culture. Some of the cells, scraped by treatment with trypsin, were inoculated as seed cells into each of the multiwell plates which were charged with the fresh preparation of the same medium and cultured. After repeating manipulations similarly as in the above and with scale up to increase the cell number, the cells were subjected to a conventional continuous culture using 50 of 150 cm$^2$ culture flasks. The resulting culture supernatants of a volume of 100 1 was collected and treated with similar methods for treating the supernatant from the cell-disruptants in Example A-1(b): salting out with ammonium sulfate, the chromatography of the solution of the precipitates using Q SEPHAROSE FF COLUMN, the chromatography of the eluted fractions using L-ASPARAGINE AGAROSE, and the chromatography of the eluted fractions using HILOAD SUPERDEX 200 COLUMN. Consequently, a purified polypeptide with a purity of 90% or more was obtained in a yield of about one µg/ml-culture.

Example A-2(c)

Physicochemical Property of Polypeptide

By testing similarly as in Example A-1(c), it was confirmed that the purified polypeptide thus obtained had equivalent physicochemical properties with the that obtained in Example A-1(b).

Example A-3(a)

Preparation of Transformant

PCRs were performed under the same conditions in Example A1(a) except for the template and the sense- and anti-sense-primers. The DNA thus obtained were treated similarly as in Example A-1(a) to prepare recombinant DNAs, "pKGPA/D364stp", "pKHA/MUT1", "pKHA/MUT2", "pKHA/MUT3" and "pKHA/MUT5". Table 5 summarizes template DNAs and nucleotide sequences of a sense-and anti-sense-primers which were used to prepare the each recombinant DNAs. By sequencing similarly as in Example A-1(a), the structures of these recombinant DNAs were confirmed as shown in FIGS. 5 to 9.

TABLE 5

| Recombinant DNA | Template DNA | Nucleotide sequences of sense (upper line) and anti-sense (lower line) primers* |
|---|---|---|
| pKGPA/D364stp | pCGPA/D364stp | 5'-GCGAATTCATGGCGCGCGCATCA-3'(SEQ ID NO:35) |
| | | 5'-GCAAGCTTTCATGCCGTGGGCAGTGT-3'(SEQ ID NO:43) |
| pKHA/MUT1 | pCHA/MUT1 | 5'-GCGAATTCATGGCGCGCGCGGTG-3'(SEQ ID NO:44) |
| | | 5'-GCAAGCTTTCACACCGAGGGTGGCGT-3'(SEQ ID NO:45) |
| pKHA/MUT2 | pCHA/MUT2 | the same as used for pKHA/MUT1 preparation |
| | | the same as used for pKHA/MUT1 preparation |
| pKHA/MUT3 | pCHA/MUT3 | the same as used for pKHA/MUT1 preparation |
| | | the same as used for pKHA/MUT1 preparation |
| pKHA/MUT5 | pCHA/MUT5 | the same as used for pKHA/MUT1 preparation |
| | | the same as used for pKHA/MUT1 preparation |

*Italics in the upper line in each column mean the 5'-terminal nucleotide sequence of a DNA encoding L-asparaginase, and those in the lower line mean the complementary sequence to the 3'-terminus of the DNA, wherein the L-asparaginese originates from a guinea pig or human.

The recombinant DNAs were treated according to the methods as in Example A1(a) to obtain transformants, "J-GPA/D364stp", "J-HA/MUT1", "J-HA/MUT2", "J-HA/MUT3" and "J-HA/MUT5".

Example A-3(b)

Production of Polypeptide

The transformants obtained in Example A-3(a) were treated according to the methods similarly as in Example A-1(b): cultivation, disrupting the resulting cells, the precipitations of the cell-disruptants with ammonium sulfate, the chromatography of the precipitate solutions using Q SEPHAROSE FF COLUMN, and the chromatography of the eluted fractions using L-ASPARAGINE AGAROSE in that order. The eluted fractions thus obtained were concentrated using membranes similarly as in Example A-1(b) followed by subjecting the chromatography using HILOAD SUPERDEX 200 COLUMN to collect the eluted fractions with a molecular weight of about 140 kDa. Each system yielded the purified polypeptide with a purity of 90% or more in a yield of about 0.1 mg/ml-culture. These purified polypeptides were analyzed by the methods as in Example A-1(c) to examine their physicochemical properties. Table 6 shows the results combined with those in Example A-1(c).

TABLE 6

| Transformant, producing the polypeptide | Molecular weight (kDa) *1 | Molecular weight (kDa) *2 | L-asparaginase activity |
|---|---|---|---|
| J-GPA/WT | about 300 | about 50 ± 10 | + |
| J-GPA/D364stp | about 140 | about 40 | + |

TABLE 6-continued

| Transformant, producing the polypeptide | Molecular weight (kDa) *1 | Molecular weight (kDa) *2 | L-asparaginase activity |
|---|---|---|---|
| J-HA/MUT1 | about 140 | about 40 | + |
| J-HA/MUT2 | about 140 | about 40 | + |
| J-HA/MUT3 | about 140 | about 40 | + |
| J-HA/MUT5 | about 140 | about 40 | + |

Note) The symbols "*1" and "*2" mean that the value was determined by gel filtration, and the value was determined by SDS-PAGE, respectively.

Table 6 indicates that all of the present polypeptides, expressed in *Escherichia coli* and purified, expressed an L-asparaginase activity. Furthermore, table 6 indicates the that the polypeptides formed tetramers.

Example A-4(a)

Preparation of Transformants

PCRs were performed under the same conditions in Example A-1(a) except for the template and the sense- and anti-sense-primers. DNAs thus obtained were ligated with the same linkers as used in Example A-2(a) under the same conditions as in Example A-2(a) to obtain recombinant DNAs, "pBIgGPA/D364stp", "pBIgHA/MUT1", "pBIgHA/MUT2", "pBIgHA/MUT3" and "pBIgHA/MUT5". Table 7 summarizes template DNAs and nucleotide sequences of sense- and anti-sense-primers which were used to prepare the each recombinant DNAs. By sequencing similarly as in Example A-1(a), the structures of these recombinant DNAs were confirmed as shown in FIGS. 10 to 14.

TABLE 7

| Recombinant DNA | Template DNA | Nucleotide sequences of sense (upper line) and anti-sense (lower line) primers* |
|---|---|---|
| pBIgGPA/D364stp | pCGPA/D364stp | 5'-GTGAATTCGGAGGTTCAGATGGCGCGCGCATCA-3'(SEQ ID NO:37) |
| | | 5'-CTGCGGCCGCTCATGCCGTGGGCAGTG-3'(SEQ ID NO:46) |
| pBIgHA/MUT1 | pCHA/MUT1 | 5'-CTGAATTCGGAGGTTCAGATGGCGCGCGCGGTG-3'(SEQ ID NO:47) |
| | | 5'-CTGCGGCCGCTCACACCGAGGGTGGCG-3'(SEQ ID NO:48) |
| pBIgHA/MUT2 | pCHA/MUT2 | the same as used for pBIgHA/MUT1 preparation |
| | | the same as used for pBIgHA/MUT1 preparation |
| pBIgHA/MUT3 | pCHA/MUT3 | the same as used for pBIgHA/MUT1 preparation |
| | | the same as used for pBIgHA/MUT1 preparation |
| pBIgHA/MUT5 | pCHA/MUT5 | the same as used for pBIgHA/MUT1 preparation |
| | | the same as used for pBIgHA/MUT1 preparation |

Note) *Italics in the upper line in each column mean the 5'-terminal nucleotide sequence of a DNA encoding L-asparaginase, and those in the lower line mean the complementary sequence to the 3'-terminus of the DNA, wherein the L-asparaginese originates from a guinea pig or human.

The recombinant DNAs thus obtained were treated similarly as in Example A-2(a) to obtain transformants, "C-GPA/D364stp", "C-HA/MUT1", "C-HA/MUT2", "C-HA/MUT3" and "C-HA/MUT5".

Example A-4(b)

Production of Polypeptide

The transformants obtained in Example A-4(a) were cultured according to the methods as in Example A-2(b), and the resulting culture supernatants were treated with similar methods for treating the supernatants from the cell-disruptants in Example A-1(b): the precipitations of culture supernatants with ammonium sulfate, the chromatography of the precipitate solutions using Q SEPHAROSE FF COLUMN, and the chromatography of the eluted fractions using L-ASPARAGINE AGAROSE in that order. The eluted fractions thus obtained were concentrated using membranes similarly as in Example A-1(b) followed by subjecting the chromatography using HILOAD SUPERDEX 200 COLUMN to collect the eluted fractions with a molecular weights of about 140 kDa. Each of these systems yielded the purified polypeptide with a purity of 90% or more in a yield of about one pg/ml-culture. These purified polypeptides were analyzed by the methods as in Example A-1(c) to examine their physicochemical properties. Table 8 shows the results combined with those in Example A-3.

TABLE 8

| The polypeptide producing transformant | Molecular weight (kDa) *1 | Molecular weight (kDa) *2 | L-asparaginase activity |
|---|---|---|---|
| J-GPA/WT | about 300 | about 50 ± 10 | + |
| J-GPA/D364stp | about 140 | about 40 | + |
| J-HA/MUT1 | about 140 | about 40 | + |
| J-HA/MUT2 | about 140 | about 40 | + |
| J-HA/MUT3 | about 140 | about 40 | + |
| J-HA/MUT5 | about 140 | about 40 | + |

Note) The symbols "*1" and "*2" mean that the value was determined by gel filtration, and the value was determined by SDS-PAGE, respectively.

Table 8 indicates that all of the present polypeptides, expressed in mammalian cells and purified, expressed an L-asparaginase activity. Furthermore, table 8 indicates the polypeptides formed tetramers.

As shown in above Example A, each of the polypeptides according to the present invention expresses an L-asparaginase activity. Therefore, the present agent for susceptive diseases hydrolyze L-asparagine in patients to exert therapeutic and preventive effects on L-asparaginase-susceptive diseases when administered to human. The wording "susceptive diseases" as referred in the present specification means diseases in general which are caused by the existence of tumor cells dependent on L-asparagine: For example, leukemias such as acute leukemia, an acute transformation of chronic leukemia and T-lymphocytic leukemia, and malignant tumors such as Hodgkin's diseases and non-Hodgkin's diseases. The present agent for susceptive diseases possesses thus the uses as anti-tumor agents for treating and/or preventing such susceptive diseases as above. Although it varies dependently on the types of agents used for such purposes and susceptive diseases to be treated, the present agent is generally processed into an agent in the form of a liquid, a paste or a solid which contains the polypeptides in an amount of 0.000001–100 w/w %, preferably, 0.0001–100 w/w %, on a dry solid basis.

The present agent can be used intact or processed into compositions by mixing with one or more selected from the group consisting of physiologically-acceptable carriers, excipients, solvents, buffers and stabilizers, and further, if necessary, other biologically-active substances and other agents. For example, "Iyakuhin-Tenkabutsu-Jiten (The Dictionary of Pharmaceutical Excipients)" (1994), edited by Japan Pharmaceutical Excipients Council, Tokyo, Japan, published by Yakujinippo LTD., Tokyo, Japan and "Iyakuhin-Tenkabutsu-Jiten-Tsuiho 1995 (Suppliment for The Dictionary of Pharmaceutical Excipients)" (1995), edited by Japan Pharmaceutical Excipients Council, Tokyo, Japan, published by Yakujinippo LTD., Tokyo, Japan, mention the embodiments of such carriers, excipients, solvents, buffers and stabilizers. Examples of such other biologically-active substances and other agents include interferon-α, interferon-β, interferon-γ, interleukin 1, interleukin 2, interleukin 3, TNF-α, TNF-β, GM-CSF, carboquone, cyclophosphamide, aclarbicin, thiotepa, busulfan, ancitabine, cytarabine, fluorouracil, 5-fluoro-1-(tetrahydro-2-furyl)uracil, methotrexate, actinomycin D, chromomycin A3, daunorubicin, doxorubicin, bleomycin, mercaptopurine, prednisolone, mitomycin C, vincristine, vinblastine, radio gold colloidal, Krestin®, picibanil, lentinan and Maruyama vaccine.

The present agent for susceptive diseases includes those in a unit dose form which means a physically separated and formed medicament suitable for administration, and contains the polypeptides in a daily dose or in a dose from 1/40 to several folds (up to 4 folds) of the daily dose. Examples of such medicaments are injections, liquids, powders, granules, tablets, capsules, sublinguals, ophthalmic solutions, nasal drops and suppositories.

The present agent can be administered to patients orally or parenterally. In both administrations, the agent exerts a satisfactory effect in the treatment and/or the prevention for the susceptive diseases. Although it varies dependently on the types of susceptive diseases and their symptoms, the agent can be orally administered to patients or parenterally administered to patients' intradermal tissues, subcutaneous tissues, muscles, and veins at a dose as amounts of the polypeptides in the range of about 0.1 $\mu$g–500 mg/shot, preferably, about 0.1–100 mg/shot, 1–4 times/day or 1–7 times/week, for one day to one year. The present agent for susceptive diseases further includes the forms by applying gene therapy. When a transformant into which the DNAs encoding the polypeptides of this invention are introduced are administered to patients to express in them, they exert equivalent effects as above administrations. For example, "Jikken-Igaku Bessatsu, Bio-manual Up Series, Idenshi-Chiryo-No-Kisogijutsu (Basic Techniques for Gene Therapy)" (1996), edited by Takashi SHIMADA, Izumi SAITO and Takaya OZAWA, published by Yodosha, Tokyo, Japan, details the general procedures for the gene therapy.

The biological activities and acute toxicity of the present polypeptides are explained based on Experiment 3 and 4 below, respectively.

EXPERIMENT 3

Biological Activity

Experiment 3-1

Antitumor Effect In Vitro

A human histocytic lymphoma cell line U937 (ATCC CRL-1593), and a cell line Molt4 (ATCC CRL-1582), derived from human T lymphoblasts, were subcultured in RPMI 1640 medium containing 10 v/v % bovine fetal serum. The cells collected by centrifugation from each subculturing system in logarithmic phase were suspended in the same medium to give a concentration of $2 \times 10^5$ cells/ml. Every one ml of the each cell suspension was charged into each of 13 wells of multiwell plates with 24 wells, "3047", commercialized by Becton Dickinson Labware, New Jersey, U.S.A After each of dilutions of 12 types of the purified polypeptides prepared in Example A-1 to A-4 with PBS was further charged into the each well, the cells were cultured at 37° C. for 72 hours in a 5 v/v % $CO_2$ incubator. The final concentration of each of the purified polypeptides was one unit/ml as an L-asparaginase activity. As a control, after charged with equivalent volume of PBS, the cells were cultured correspondingly. The cells were collected after the cultivation to stain cells died with trypan blue. Cell survival ratio in each systems with the purified polypeptides was compared with that in the control. All of the cell survival ratios with the purified polypeptides were significantly lower than that in the control. These results indicate that all of the present polypeptides, obtained in Examples A-1 to A-4,have cytotoxicity to U937 and Molt4.

Experiment 3-2

Antitumor Effect In Vivo

For model mice were used C3H mice wherein a mouse lymphoma cell line 6C3HED, registered in Cell Resource Center for Biomedical Research, Institute of Development Aging and Cancer, Tohoku University, Sendai, Japan, was transplanted with passages by subcutaneous injections at their sides in a range of $1\times10^7$ cells/body every 8 days in usual manner. To the model mice were administered the purified polypeptides obtained in Example A-1 to A-4 in the range of 400 unit/body by venoclyses every day from fourth to seventh days after transplanted with the cells. Dimensions of the tumors were observed with naked eyes on fourth and eighth day after the transplantations. The purified polypeptides were administered after diluted with 0.15 M NaCl and filtrated with membrane filters, 0.45 μm in pore size, commercialized by Millipore Corp., Bedford, U.S.A. As a control, 0.15 M NaCl was treated correspondingly. While significant enlargements of the tumors were observed in the control, significant involutions or disappearances of the tumors were observed in mice administered with the polypeptides. These results indicates that all of the present polypeptides, obtained. in Examples A-1 to A-4, are able to cure the tumors of model mice.

EXPERIMENT 4

Acute Toxicity

The purified polypeptides obtained in Examples A-1 to A-4 were separately administered to 8-week-old mice percutaneously, perorally or intraperitoneally according to conventional manner. The $LD_{50}$ of all the polypeptides was about 100 mg/kg or higher independently of the administration routes. These results evidenced that the present polypeptides could be safely incorporated into pharmaceuticals for administering human.

The following examples explain the present agent for susceptive diseases.

Example B-1

Solution

The purified polypeptides obtained in Examples A-1 to A-4 were separately dissolved to give a concentration of 0.1 mg/ml in physiological saline containing one w/v % human serum albumin as a stabilizer, and sterilized with membrane filters according to conventional manner to obtain solutions.

All of the products have satisfactory stabilities and can be used as injections, ophthalmic solutions, collunarium in the treatment and/or the prevention of susceptive diseases including a malignant tumor, acute leukemia, malignant lymphoma, an acute transformation of chronic leukemia, T-lymphocytic leukemia.

Example B-2

Solution

The purified polypeptides obtained in Examples A-1 to A-4 were separately dissolved to give a concentration of 0.1 mg/ml in physiological saline containing one w/v % glycerol as a stabilizer, and sterilized with membrane filters according to conventional manner to obtain solutions.

All of the products have satisfactory stabilities and can be used as injections, ophthalmic solutions, collunarium for the treatment and/or the prevention of susceptive diseases including a malignant tumor, acute leukemia, malignant lymphoma, an acute transformation of chronic leukemia and T-lymphocytic leukemia.

Example B-3

Dry injection

The purified polypeptides obtained in Examples A-1 to A-4 were separately dissolved to give a concentration of 50 mg/ml in physiological saline containing one w/v % purified gelatin as a stabilizer, and the solutions were sterilized with membrane filters according to conventional manner. One ml aliquots of the sterilized solutions were distributed to vials, lyophilized and cap sealed.

All of the products have satisfactory stabilities and can be used as dry injections for the treatment and/or the prevention of susceptive diseases including a malignant tumor, acute leukemia, malignant lymphoma, an acute transformation of chronic leukemia and T-lymphocytic leukemia.

Example B-4

Ointment

"HI-BIS-WAKO 104", a carboxyvinyl polymer commercialized by Wako Pure Chemicals, Tokyo, Japan, and a purified trehalose were dissolved in sterilized distilled water to give concentrations of 1.4 w/w % and 2. 0 w/w %, respectively, and the purified polypeptides obtained in Examples A-1 to A-4 were separately mixed to homogeneity in the solutions followed by adjusting the pH of the resulting solutions to pH 7.2 to obtain pastes containing about one mg/g of the polypeptides.

All of the products have satisfactory spreadabilities and stabilities, and can be used as ointments for treating and/or preventing susceptive diseases including a malignant tumor, acute leukemia, malignant lymphoma, an acute transformation of chronic leukemia and T-lymphocytic leukemia.

Example B-5

Tablet

Any one of the purified polypeptides obtained in Examples A-1 to A-4 and LUMIN, i.e. [bis-4-(1-ethylquinoline)] [γ-4'-(1-ethylquinoline] pentamethionine cyanine, as a cell activator were mixed to homogeneity with "FINETOSE®", an hydrous crystalline α-maltose commercialized by Hayashibara Co., Ltd., Okayama, Japan, and the mixtures were tabletted by tabletting machine to obtain tablets, about 200 mg weight each, containing the polypeptide and the LUMIN, about 5 mg each.

All of the products have satisfactory swallowing abilities, stabilities and cell activating activities, and can be used for treating and/or preventing susceptive diseases including a malignant tumor, acute leukemia, malignant lymphoma, an acute transformation of chronic leukemia and T-lymphocytic leukemia.

The present invention is based on the findings of polypeptides which originate from mammal, having L-asparaginase activity. The polypeptides are substances which have revealed amino acid sequences totally, and stable activities to hydrolyze L-asparagine. Therefore, the polypeptides exert satisfactory effects in the treatment and/or the prevention for diseases caused by tumor cells dependent on L-asparagine.

The polypeptides originate from mammal, so that they have low antigenicities to human and don't cause serious side effects even when administered in large amounts or continuously. Therefore, the polypeptides have the advantage that they can exert desired effects without restricted controls on patients' sensitivities.

The polypeptides thus valuable can be produced in desired amounts using the present DNAs encoding them.

Thus, the present invention is a significant invention which has a remarkable effect and gives a great contribution to this field.

While there has been described what is at present considered to be the preferred embodiments of the present invention, it will be understood the various modifications may be made therein, and it is intended to cover in the appended claims all such modifications as fall within the true spirits and scope of the invention.

We claim:

1. A purified polypeptide or a fragment thereof exhibiting L-asparaginase activity, wherein said polypeptide consists of an amino acid sequence selected from the group consisting of SEQ ID NOs:4, 6, 7, 8, and 9.

2. The purified polypeptide of claim 1, whose enzymatically active form is an oligomeric form.

3. A pharmaceutical composition, comprising the purified polypeptide of claim 1, as an effective ingredient and a pharmaceutically-acceptable diluent, excipient, carrier or auxiliary agent.

4. The pharmaceutical composition according to claim 3, which is used to treat malignant tumors, leukemias and lymphomas.

5. The pharmaceutical composition according to claim 3, further comprising one or more members selected from the group consisting of serum albumin, glycerol, gelatin, trehalose and maltose as a stabilizer.

* * * * *

```
                         SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
         (A) LENGTH:4 amino acids
         (B) TYPE:amino acid
         (C) STRANDEDNESS: single
         (D) TOPOLOGY:linear (ii) MOLECULE TYPE:peptide (xi) SEQUENCE DESCRIPTION:SEQ ID NO:1:

Thr Gly Gly Thr
1

(2) INFORMATION FOR SEQ ID NO:2:

(i) SEQUENCE CHARACTERISTICS:
         (A) LENGTH:5 amino acids
         (B) TYPE:amino acid
         (C) STRANDEDNESS: single
         (D) TOPOLOGY:linear (ii) MOLECULE TYPE:peptide (xi) SEQUENCE DESCRIPTION:SEQ ID NO:2:

His Gly Thr Asp Thr
1               5

(2) INFORMATION FOR SEQ ID NO:3:

(i) SEQUENCE CHARACTERISTICS:
         (A) LENGTH:5 amino acids
         (B) TYPE:amino acid
         (C) STRANDEDNESS: single
         (D) TOPOLOGY:linear (ii) MOLECULE TYPE:peptide (xi) SEQUENCE DESCRIPTION:SEQ ID NO:3:

Gln Cys Leu Xaa Gly
1               5

(2) INFORMATION FOR SEQ ID NO:4:

(i) SEQUENCE CHARACTERISTICS:
         (A) LENGTH:363 amino acids
         (B) TYPE:amino acid
         (C) STRANDEDNESS: single
         (D) TOPOLOGY:linear (ii) MOLECULE TYPE:peptide
```

(xi) SEQUENCE DESCRIPTION:SEQ ID NO:4:

```
Met Ala Arg Ala Ser Gly Ser Glu Arg His Leu Leu Ile Tyr Thr
1               5                   10                  15

Gly Gly Thr Leu Gly Met Gln Ser Lys Gly Gly Val Leu Val Pro Gly
                20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Phe Gly Ala Ser Met Leu Ser Phe
            115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Lys Phe Glu Ala Phe Cys Ser Pro Asn Leu Ser Pro Leu Ala Thr Val
    195                 200                 205

Gly Ala Asp Val Thr Ile Ala Trp Asp Leu Val Arg Lys Val Asn Trp
210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Ala Gln
            275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Gly Arg Arg Gln Glu Leu Leu Ala Lys
                340                 345                 350

Asp Leu Arg Gly Glu Met Thr Leu Pro Thr Ala
            355                 360     363
```

(2) INFORMATION FOR SEQ ID NO:5:

(i) SEQUENCE CHARACTERISTICS:
      (A) LENGTH:565 amino acids
      (B) TYPE:amino acid
      (D) TOPOLOGY:linear (ii) MOLECULE TYPE:peptide (xi) SEQUENCE DESCRIPTION:SEQ ID NO:5:

```
Met Ala Arg Ala Ser Gly Ser Glu Arg His Leu Leu Ile Tyr Thr
1               5                   10                  15

Gly Gly Thr Leu Gly Met Gln Ser Lys Gly Val Leu Val Pro Gly
                20                  25                  30

Pro Gly Leu Val Thr Leu Arg Thr Leu Pro Met Phe His Asp Lys
                35                  40              45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Phe Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Asn Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr Leu Gly Gln Gly Val Ala Arg Leu Phe Ser
    370                 375                 380

Leu Phe Gly Cys Gln Glu Glu Asp Ser Val Gln Asp Ala Val Met Pro
385                 390                 395                 400
```

```
Ser Leu Ala Leu Ala Leu Ala His Ala Gly Glu Leu Glu Ala Leu Gln
            405                 410                 415

Ala Leu Met Glu Leu Gly Ser Asp Leu Arg Leu Lys Asp Ser Asn Gly
            420                 425                 430

Gln Thr Leu Leu His Val Ala Ala Arg Asn Gly Arg Asp Gly Val Val
            435                 440                 445

Thr Met Leu Leu His Arg Gly Met Asp Val Asn Ala Arg Asp Arg Asp
            450                 455                 460

Gly Leu Ser Pro Leu Leu Leu Ala Val Gln Gly Arg His Arg Glu Cys
465                 470                 475                 480

Ile Arg Leu Leu Arg Lys Ala Gly Ala Cys Leu Ser Pro Gln Asp Leu
            485                 490                 495

Lys Asp Ala Gly Thr Glu Leu Cys Arg Leu Ala Ser Arg Ala Asp Met
            500                 505                 510

Glu Gly Leu Gln Ala Trp Gly Gln Ala Gly Ala Asp Leu Gln Gln Pro
            515                 520                 525

Gly Tyr Asp Gly Arg Ser Ala Leu Cys Val Ala Glu Ala Ala Gly Asn
            530                 535                 540

Gln Glu Val Leu Ala Leu Leu Arg Asn Leu Ala Leu Val Gly Pro Glu
545                 550                 555                 560

Val Pro Pro Ala Ile
            565

(2) INFORMATION FOR SEQ ID NO:6:

(i) SEQUENCE CHARACTERISTICS:
        (A) LENGTH:365 amino acids
        (B) TYPE:amino acid
        (C) STRANDEDNESS: single
        (D) TOPOLOGY:linear (ii) MOLECULE TYPE:peptide (xi) SEQUENCE DESCRIPTION:SEQ ID NO:6:

Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
            85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
            115                 120                 125

Met Leu Glu Asn Leu Gln Lys Thr Val Ile Leu Thr Gly Ala Gln Val
            130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
            165                 170                 175
```

```
Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
            195                 200                 205

Gly Ala Asp Ile Thr Ile Asn Arg Glu Leu Val Arg Lys Val Asp Gly
            210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
            275                 280                 285

Arg Gly Leu Val Ile Val Asn Cys Thr Gln Cys Leu Arg Gly Ala Val
            290                 295                 300

Thr Thr Asp Tyr Ala Ala Gly Met Ala Met Ala Gly Ala Asn Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val
            355                 360                 365

(2) INFORMATION FOR SEQ ID NO:7:

(i) SEQUENCE CHARACTERISTICS:
        (A) LENGTH:365 amino acids
        (B) TYPE:amino acid
        (C) STRANDEDNESS: single
        (D) TOPOLOGY:linear (ii) MOLECULE TYPE:peptide (xi) SEQUENCE DESCRIPTION:SEQ ID NO:7:

Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
        50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
            115                 120                 125

Met Leu Glu Asn Leu Gln Lys Thr Val Ile Leu Thr Gly Ala Gln Val
            130                 135                 140

Pro Ile His Ala Leu Trp Ser Asp Gly Arg Glu Asn Leu Leu Gly Ala
145                 150                 155                 160
```

```
Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
            195                 200                 205

Gly Ala Asp Ile Thr Ile Asn Arg Glu Leu Val Arg Lys Val Asp Gly
            210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
                260                 265                 270

Gly Pro Thr Lys Pro Asp Leu Leu Gln Glu Leu Arg Val Ala Thr Glu
                275                 280                 285

Arg Gly Leu Val Ile Val Asn Cys Thr Gln Cys Leu Arg Gly Ala Val
            290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
                340                 345                 350

Thr Lys Asp Leu Arg Gly Glu Met Thr Pro Pro Ser Val
                355                 360                 365

(2) INFORMATION FOR SEQ ID NO:8:

(i) SEQUENCE CHARACTERISTICS:
        (A) LENGTH:365 amino acids
        (B) TYPE:amino acid
        (C) STRANDEDNESS: single
        (D) TOPOLOGY:linear (ii) MOLECULE TYPE:peptide (xi) SEQUENCE DESCRIPTION:SEQ ID NO:8:

Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
                20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
            115                 120                 125

Met Leu Glu Asn Leu Gln Lys Thr Val Ile Leu Thr Gly Ala Gln Val
130                 135                 140
```

```
Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
            165                 170                 175

Gln Asn Gln Leu Phe Arg Gly Asn Arg Ala Thr Lys Val Asp Ala Arg
        180                 185                 190

Arg Phe Ala Ala Phe Cys Ser Pro Asn Leu Leu Pro Leu Ala Thr Val
    195                 200                 205

Gly Ala Asp Ile Thr Ile Asn Arg Glu Leu Val Arg Lys Val Asp Gly
210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr Gln Cys Leu Gln Gly Ala Val
    290                 295                 300

Thr Thr Asp Tyr Ala Ala Gly Met Ala Met Ala Gly Ala Asn Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val
        355                 360                 365

(2) INFORMATION FOR SEQ ID NO:9:

(i) SEQUENCE CHARACTERISTICS:
        (A) LENGTH:365 amino acids
        (B) TYPE:amino acid
        (C) STRANDEDNESS: single
        (D) TOPOLOGY:linear (ii) MOLECULE TYPE:peptide (xi) SEQUENCE DESCRIPTION:SEQ ID NO:9:

Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
        35                  40                  45

Glu His Ala Arg Ala Arg Gly Leu Ser Glu Asp Thr Leu Val Leu Pro
    50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
            85                  90                  95

Ala Gln Thr Ile Lys Arg His Tyr Glu Gln Tyr His Gly Phe Val Val
        100                 105                 110

Ile His Gly Thr Asp Thr Met Ala Phe Ala Ala Ser Met Leu Ser Phe
    115                 120                 125
```

```
Met Leu Glu Asn Leu Gln Lys Thr Val Ile Leu Thr Gly Ala Gln Val
    130                 135                 140
Pro Ile His Ala Leu Trp Ser Asp Gly Arg Glu Asn Leu Leu Gly Ala
145                 150                 155                 160
Leu Leu Met Ala Gly Gln Tyr Val Ile Pro Glu Val Cys Leu Phe Phe
                165                 170                 175
Gln Asn Gln Leu Phe Arg Gly Asn Arg Ala Thr Lys Val Asp Ala Arg
                180                 185                 190
Arg Phe Ala Ala Phe Cys Ser Pro Asn Leu Leu Pro Leu Ala Thr Val
                195                 200                 205
Gly Ala Asp Ile Thr Ile Asn Arg Glu Leu Val Arg Lys Val Asp Gly
210                 215                 220
Lys Ala Gly Leu Val Val His Ser Ser Met Glu Gln Asp Val Gly Leu
225                 230                 235                 240
Leu Arg Leu Tyr Pro Gly Ile Pro Ala Ala Leu Val Arg Ala Phe Leu
                245                 250                 255
Gln Pro Pro Leu Lys Gly Val Val Met Glu Thr Phe Gly Ser Gly Asn
                260                 265                 270
Gly Pro Thr Lys Pro Asp Leu Leu Gln Glu Leu Arg Val Ala Thr Glu
                275                 280                 285
Arg Gly Leu Val Ile Val Asn Cys Thr Gln Cys Leu Gln Gly Ala Val
    290                 295                 300
Thr Thr Asp Tyr Ala Ala Gly Met Ala Met Ala Gly Ala Gly Val Ile
305                 310                 315                 320
Ser Gly Phe Asp Met Thr Ser Glu Ala Ala Leu Ala Lys Leu Ser Tyr
                325                 330                 335
Val Leu Gly Gln Pro Gly Leu Ser Leu Asp Val Arg Lys Glu Leu Leu
                340                 345                 350
Thr Lys Asp Leu Arg Gly Glu Met Thr Pro Pro Ser Val
                355                 360                 365

(2) INFORMATION FOR SEQ ID NO:10:

(i) SEQUENCE CHARACTERISTICS:
        (A) LENGTH:1089 base pairs
        (B) TYPE:nucleic acid
        (C) STRANDEDNESS: single
        (D) TOPOLOGY:linear (xi) SEQUENCE DESCRIPTION:SEQ ID NO:10:

ATGGCGCGCG CATCAGGCTC CGAGAGGCAC CTGCTGCTCA TCTACACTGG CGGCACTTTG      60

GGCATGCAGA GCAAGGGCGG GGTGCTCGTC CCCGGCCCAG GCCTGGTCAC TCTGCTGCGG     120

ACCCTGCCCA TGTTCCATGA CAAGGAGTTC GCCCAGGCCC AGGGCCTCCC TGACCATGCT     180

CTGGCGCTGC CCCCTGCCAG CCACGGCCCC AGGGTCCTCT ACACGGTGCT GGAGTGCCAG     240

CCCCTCTTGG ATTCCAGCGA CATGACCATC GATGATTGGA TTCGCATAGC AAGATCATA     300

GAGAGGCACT ATGAGCAGTA CCAAGGCTTT GTGGTTATCC ACGGCACCGA CACCATGGCC     360

TTTGGGGCCT CCATGCTGTC CTTCATGCTG GAAAACCTGC ACAAACCAGT CATCCTCACT     420

GGCGCCCAGG TGCCAATCCG TGTGCTGTGG AATGACGCCC GGGAAAACCT GCTGGGGGCG     480

TTGCTTGTGG CCGGCCAATA CATCATCCCT GAGGTCTGCC TGTTTATGAA CAGTCAGCTG     540

TTTCGGGGAA ACCGGGTAAC CAAGGTGGAC TCCCAGAAGT TGAGGCCTT CTGCTCCCCC      600

AATCTGTCCC CACTAGCCAC TGTGGGCGCG GATGTCACAA TTGCCTGGGA CCTGGTGCGC     660
```

```
AAGGTCAACT GGAAGGACCC GCTGGTGGTG CACAGCAACA TGGAGCACGA CGTGGCACTG      720

CTGCGCCTCT ACCCTGGCAT CCCGGCCTCC CTGGTCCGGG CATTCCTGCA GCCCCCGCTC      780

AAGGGCGTGG TCCTGGAGAC CTTCGGCTCT GGCAACGGGC CGAGCAAGCC CGACCTGCTG      840

CAGGAGTTGC GGGCCGCGGC CCAGCGCGGC CTCATCATGG TCAACTGCAG CCAGTGCCTG      900

CGGGGGTCTG TGACCCCGGG CTATGCCACG AGCTTGGCGG GCGCCAACAT CGTGTCCGGC      960

TTAGACATGA CCTCAGAGGC CGCGCTGGCT AAGCTGTCCT ACGTGTTGGG CCTGCCGGAG     1020

CTGAGCCTGG AGCGCAGGCA GGAGCTGCTG GCCAAGGATC TTCGCGGGGA AATGACACTG     1080

CCCACGGCA                                                            1089
```

(2) INFORMATION FOR SEQ ID NO:11:

(i) SEQUENCE CHARACTERISTICS:
        (A) LENGTH:1095 base pairs
        (B) TYPE:nucleic acid
        (C) STRANDEDNESS: single
        (D) TOPOLOGY:linear (xi) SEQUENCE DESCRIPTION:SEQ ID NO:11:

```
ATGGCGCGCG CGGTGGGGCC CGAGCGGAGG CTGCTGGCCG TCTACACCGG CGGCACCATT       60

GGCATGCGGA GTGAGCTCGG CGTGCTTGTG CCCGGGACGG GCCTGGCTGC CATCCTGAGG      120

ACACTGCCCA TGTTCCATGA CGAGGAGCAC GCCCGAGCCC GCGGCCTCTC TGAGGACACC      180

CTGGTGCTAC CCCCGGACAG CCGCAACCAG AGGATCCTCT ACACCGTGCT GGAGTGCCAG      240

CCCCTCTTCG ACTCCAGTGA CATGACCATC GCTGAGTGGG TTCGCGTTGC CCAGACCATC      300

AAGAGGCACT ACGAGCAGTA CCACGGCTTT GTGGTCATCC ACGGCACCGA CACCATGGCC      360

TTTGCTGCCT CGATGCTGTC CTTCATGCTG GAGAACCTGC AGAAGACTGT CATCCTCACT      420

GGGGCCCAGG TGCCCATCCA TGCCCTGTGG AGCGACGGCC GTGAGAACCT GCTGGGGGCA      480

CTGCTCATGG CTGGCCAGTA TGTGATCCCA GAGGTCTGCC TTTTCTTCCA GAATCAGCTG      540

TTTCGGGGCA ACCGGGCAAC CAAGGTAGAC GCTCGGAGGT TCGCAGCTTT CTGCTCCCCG      600

AACCTGCTGC CTCTGGCCAC AGTGGGTGCT GACATCACAA TCAACAGGGA GCTGGTGCGG      660

AAGGTGGACG GGAAGGCTGG GCTGGTGGTG CACAGCAGCA TGGAGCAGGA CGTGGGCCTG      720

CTGCGCCTCT ACCCTGGGAT CCCTGCCGCC CTGGTTCGGG CCTTCTTGCA GCCTCCCCTG      780

AAGGGCGTGG TCATGGAGAC CTTCGGTTCA GGGAACGGAC CCACCAAGCC CGACCTGCTG      840

CAGGAGCTGC GGGTGGCCAC CGAGCGCGGC CTGGTCATCG TCAACTGTAC CCAGTGCCTC      900

CGGGGGGCTG TGACCACAGA CTATGCAGCT GGCATGGCCA TGGCGGGAGC CAACGTCATC      960

TCAGGCTTCG ACATGACATC GGAGGCCGCC CTGGCCAAGC TATCGTATGT GCTGGGCCAG     1020

CCAGGGCTGA GCCTGGATGT CAGGAAGGAG CTGCTGACCA AGGACTTCG GGGGGAGATG     1080

ACGCCACCCT CGGTG                                                     1095
```

(2) INFORMATION FOR SEQ ID NO:12:

(i) SEQUENCE CHARACTERISTICS:
        (A) LENGTH:1095 base pairs
        (B) TYPE:nucleic acid
        (C) STRANDEDNESS: single
        (D) TOPOLOGY:linear (xi) SEQUENCE DESCRIPTION:SEQ ID NO:12:

```
ATGGCGCGCG CGGTGGGGCC CGAGCGGAGG CTGCTGGCCG TCTACACCGG CGGCACCATT       60

GGCATGCGGA GTGAGCTCGG CGTGCTTGTG CCCGGGACGG GCCTGGCTGC CATCCTGAGG      120
```

| ACACTGCCCA | TGTTCCATGA | CGAGGAGCAC | GCCCGAGCCC | GCGGCCTCTC | TGAGGACACC | 180 |
| CTGGTGCTAC | CCCCGGACAG | CCGCAACCAG | AGGATCCTCT | ACACCGTGCT | GGAGTGCCAG | 240 |
| CCCCTCTTCG | ACTCCAGTGA | CATGACCATC | GCTGAGTGGG | TTCGCGTTGC | CCAGACCATC | 300 |
| AAGAGGCACT | ACGAGCAGTA | CCACGGCTTT | GTGGTCATCC | ACGGCACCGA | CACCATGGCC | 360 |
| TTTGCTGCCT | CGATGCTGTC | CTTCATGCTG | GAGAACCTGC | AGAAGACTGT | CATCCTCACT | 420 |
| GGGGCCCAGG | TGCCCATCCA | TGCCCTGTGG | AGCGACGGCC | GTGAGAACCT | GCTGGGGGCA | 480 |
| CTGCTCATGG | CTGGCCAGTA | TGTGATCCCA | GAGGTCTGCC | TTTTCTTCCA | GAATCAGCTG | 540 |
| TTTCGGGGCA | ACCGGGCAAC | CAAGGTAGAC | GCTCGGAGGT | TCGCAGCTTT | CTGCTCCCCG | 600 |
| AACCTGCTGC | CTCTGGCCAC | AGTGGGTGCT | GACATCACAA | TCAACAGGGA | GCTGGTGCGG | 660 |
| AAGGTGGACG | GGAAGGCTGG | GCTGGTGGTG | CACAGCAGCA | TGGAGCAGGA | CGTGGGCCTG | 720 |
| CTGCGCCTCT | ACCCTGGGAT | CCCTGCCGCC | CTGGTTCGGG | CCTTCTTGCA | GCCTCCCCTG | 780 |
| AAGGGCGTGG | TCATGGAGAC | CTTCGGTTCA | GGGAACGGAC | CCACCAAGCC | CGACCTGCTG | 840 |
| CAGGAGCTGC | GGGTGGCCAC | CGAGCGCGGC | CTGGTCATCG | TCAACTGTAC | CCAGTGCCTC | 900 |
| CGGGGGGCTG | TGACCACAGA | CTATGCAGCT | GGCATGGCCA | TGGCGGGAGC | CGGCGTCATC | 960 |
| TCAGGCTTCG | ACATGACATC | GGAGGCCGCC | CTGGCCAAGC | TATCGTATGT | GCTGGGCCAG | 1020 |
| CCAGGGCTGA | GCCTGGATGT | CAGGAAGGAG | CTGCTGACCA | AGGACCTTCG | GGGGGAGATG | 1080 |
| ACGCCACCCT | CGGTG | | | | | 1095 |

(2) INFORMATION FOR SEQ ID NO:13:

(i) SEQUENCE CHARACTERISTICS:
        (A) LENGTH:1095 base pairs
        (B) TYPE:nucleic acid
        (C) STRANDEDNESS: single
        (D) TOPOLOGY:linear (xi) SEQUENCE DESCRIPTION:SEQ ID NO:13:

| ATGGCGCGCG | CGGTGGGGCC | CGAGCGGAGG | CTGCTGGCCG | TCTACACCGG | CGGCACCATT | 60 |
| GGCATGCGGA | GTGAGCTCGG | CGTGCTTGTG | CCCGGGACGG | GCCTGGCTGC | CATCCTGAGG | 120 |
| ACACTGCCCA | TGTTCCATGA | CGAGGAGCAC | GCCCGAGCCC | GCGGCCTCTC | TGAGGACACC | 180 |
| CTGGTGCTAC | CCCCGGACAG | CCGCAACCAG | AGGATCCTCT | ACACCGTGCT | GGAGTGCCAG | 240 |
| CCCCTCTTCG | ACTCCAGTGA | CATGACCATC | GCTGAGTGGG | TTCGCGTTGC | CCAGACCATC | 300 |
| AAGAGGCACT | ACGAGCAGTA | CCACGGCTTT | GTGGTCATCC | ACGGCACCGA | CACCATGGCC | 360 |
| TTTGCTGCCT | CGATGCTGTC | CTTCATGCTG | GAGAACCTGC | AGAAGACTGT | CATCCTCACT | 420 |
| GGGGCCCAGG | TGCCCATCCA | TGCCCTGTGG | AGCGACGGCC | GTGAGAACCT | GCTGGGGGCA | 480 |
| CTGCTCATGG | CTGGCCAGTA | TGTGATCCCA | GAGGTCTGCC | TTTTCTTCCA | GAATCAGCTG | 540 |
| TTTCGGGGCA | ACCGGGCAAC | CAAGGTAGAC | GCTCGGAGGT | TCGCAGCTTT | CTGCTCCCCG | 600 |
| AACCTGCTGC | CTCTGGCCAC | AGTGGGTGCT | GACATCACAA | TCAACAGGGA | GCTGGTGCGG | 660 |
| AAGGTGGACG | GGAAGGCTGG | GCTGGTGGTG | CACAGCAGCA | TGGAGCAGGA | CGTGGGCCTG | 720 |
| CTGCGCCTCT | ACCCTGGGAT | CCCTGCCGCC | CTGGTTCGGG | CCTTCTTGCA | GCCTCCCCTG | 780 |
| AAGGGCGTGG | TCATGGAGAC | CTTCGGTTCA | GGGAACGGAC | CCACCAAGCC | CGACCTGCTG | 840 |
| CAGGAGCTGC | GGGTGGCCAC | CGAGCGCGGC | CTGGTCATCG | TCAACTGTAC | CCAGTGCCTC | 900 |
| CAGGGGGCTG | TGACCACAGA | CTATGCAGCT | GGCATGGCCA | TGGCGGGAGC | CAACGTCATC | 960 |
| TCAGGCTTCG | ACATGACATC | GGAGGCCGCC | CTGGCCAAGC | TATCGTATGT | GCTGGGCCAG | 1020 |

| CCAGGGCTGA GCCTGGATGT CAGGAAGGAG CTGCTGACCA AGGACCTTCG GGGGAGATG | 1080 |
| ACGCCACCCT CGGTG | 1095 |

(2) INFORMATION FOR SEQ ID NO:14:

(i) SEQUENCE CHARACTERISTICS:
        (A) LENGTH:1095 base pairs
        (B) TYPE:nucleic acid
        (C) STRANDEDNESS: single
        (D) TOPOLOGY:linear (xi) SEQUENCE DESCRIPTION:SEQ ID NO:14:

| ATGGCGCGCG CGGTGGGGCC CGAGCGGAGG CTGCTGGCCG TCTACACCGG CGGCACCATT | 60 |
| GGCATGCGGA GTGAGCTCGG CGTGCTTGTG CCCGGGACGG GCCTGGCTGC CATCCTGAGG | 120 |
| ACACTGCCCA TGTTCCATGA CGAGGAGCAC GCCCGAGCCC GCGGCCTCTC TGAGGACACC | 180 |
| CTGGTGCTAC CCCCGGACAG CCGCAACCAG AGGATCCTCT ACACCGTGCT GGAGTGCCAG | 240 |
| CCCCTCTTCG ACTCCAGTGA CATGACCATC GCTGAGTGGG TTCGCGTTGC CCAGACCATC | 300 |
| AAGAGGCACT ACGAGCAGTA CCACGGCTTT GTGGTCATCC ACGGCACCGA CACCATGGCC | 360 |
| TTTGCTGCCT CGATGCTGTC CTTCATGCTG GAGAACCTGC AGAAGACTGT CATCCTCACT | 420 |
| GGGGCCCAGG TGCCCATCCA TGCCCTGTGG AGCGACGGCC GTGAGAACCT GCTGGGGGCA | 480 |
| CTGCTCATGG CTGGCCAGTA TGTGATCCCA GAGGTCTGCC TTTTCTTCCA GAATCAGCTG | 540 |
| TTTCGGGGCA ACCGGGCAAC CAAGGTAGAC GCTCGGAGGT TCGCAGCTTT CTGCTCCCCG | 600 |
| AACCTGCTGC CTCTGGCCAC AGTGGGTGCT GACATCACAA TCAACAGGGA GCTGGTGCGG | 660 |
| AAGGTGGACG GGAAGGCTGG GCTGGTGGTG CACAGCAGCA TGGAGCAGGA CGTGGGCCTG | 720 |
| CTGCGCCTCT ACCCTGGGAT CCCTGCCGCC CTGGTTCGGG CCTTCTTGCA GCCTCCCCTG | 780 |
| AAGGGCGTGG TCATGGAGAC CTTCGGTTCA GGGAACGGAC CCACCAAGCC CGACCTGCTG | 840 |
| CAGGAGCTGC GGGTGGCCAC CGAGCGCGGC CTGGTCATCG TCAACTGTAC CCAGTGCCTC | 900 |
| CAGGGGGCTG TGACCACAGA CTATGCAGCT GGCATGGCCA TGGCGGGAGC CGGCGTCATC | 960 |
| TCAGGCTTCG ACATGACATC GGAGGCCGCC CTGGCCAAGC TATCGTATGT GCTGGGCCAG | 1020 |
| CCAGGGCTGA GCCTGGATGT CAGGAAGGAG CTGCTGACCA AGGACCTTCG GGGGAGATG | 1080 |
| ACGCCACCCT CGGTG | 1095 |

(2) INFORMATION FOR SEQ ID NO:15:

(i) SEQUENCE CHARACTERISTICS:
        (A) LENGTH:1928 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:guinea pig
        (F) TISSUE TYPE:liver (iX) FEATURE:
        (A) NAME/KEY:5'UTR
        (B) LOCATION:1..19
        (C) IDENTIFICATION METHOD:S
        (A) NAME/KEY:mat peptide
        (B) LOCATION:20..1714

(C) IDENTIFICATION METHOD:S
(A) NAME/KEY:3'UTR
(B) LOCATION:1715..1928
(C) IDENTIFICATION METHOD:S (xi) SEQUENCE DESCRIPTION: SEQ ID NO:15:

| | | | | | | | | | | | | | | | |
|---|---|---|---|---|---|---|---|---|---|---|---|---|---|---|---|
| GAGTGGCTTA | GCCGCAGGC | ATG | GCG | CGC | GCA | TCA | GGC | TCC | GAG | AGG | CAC | | | | 49 |
| | | Met | Ala | Arg | Ala | Ser | Gly | Ser | Glu | Arg | His | | | | |
| | | 1 | | | 5 | | | | | | 10 | | | | |
| CTG | CTG | CTC | ATC | TAC | ACT | GGC | GGC | ACT | TTG | GGC | ATG | CAG | AGC | AAG GGC | 97 |
| Leu | Leu | Leu | Ile | Tyr | Thr | Gly | Gly | Thr | Leu | Gly | Met | Gln | Ser | Lys Gly | |
| | | | 15 | | | | | 20 | | | | | 25 | | |
| GGG | GTG | CTC | GTC | CCC | GGC | CCA | GGC | CTG | GTC | ACT | CTG | CTG | CGG | ACC CTG | 145 |
| Gly | Val | Leu | Val | Pro | Gly | Pro | Gly | Leu | Val | Thr | Leu | Leu | Arg | Thr Leu | |
| | | 30 | | | | | 35 | | | | | 40 | | | |
| CCC | ATG | TTC | CAT | GAC | AAG | GAG | TTC | GCC | CAG | GCC | CAG | GGC | CTC | CCT GAC | 193 |
| Pro | Met | Phe | His | Asp | Lys | Glu | Phe | Ala | Gln | Ala | Gln | Gly | Leu | Pro Asp | |
| | | 45 | | | | 50 | | | | | 55 | | | | |
| CAT | GCT | CTG | GCG | CTG | CCC | CCT | GCC | AGC | CAC | GGC | CCC | AGG | GTC | CTC TAC | 241 |
| His | Ala | Leu | Ala | Leu | Pro | Pro | Ala | Ser | His | Gly | Pro | Arg | Val | Leu Tyr | |
| | 60 | | | | 65 | | | | | 70 | | | | | |
| ACG | GTG | CTG | GAG | TGC | CAG | CCC | CTC | TTG | GAT | TCC | AGC | GAC | ATG | ACC ATC | 289 |
| Thr | Val | Leu | Glu | Cys | Gln | Pro | Leu | Leu | Asp | Ser | Ser | Asp | Met | Thr Ile | |
| 75 | | | | 80 | | | | | 85 | | | | | 90 | |
| GAT | GAT | TGG | ATT | CGC | ATA | GCC | AAG | ATC | ATA | GAG | AGG | CAC | TAT | GAG CAG | 337 |
| Asp | Asp | Trp | Ile | Arg | Ile | Ala | Lys | Ile | Ile | Glu | Arg | His | Tyr | Glu Gln | |
| | | | 95 | | | | | 100 | | | | | 105 | | |
| TAC | CAA | GGC | TTT | GTG | GTT | ATC | CAC | GGC | ACC | GAC | ACC | ATG | GCC | TTT GGG | 385 |
| Tyr | Gln | Gly | Phe | Val | Val | Ile | His | Gly | Thr | Asp | Thr | Met | Ala | Phe Gly | |
| | | 110 | | | | | 115 | | | | | 120 | | | |
| GCC | TCC | ATG | CTG | TCC | TTC | ATG | CTG | GAA | AAC | CTG | CAC | AAA | CCA | GTC ATC | 433 |
| Ala | Ser | Met | Leu | Ser | Phe | Met | Leu | Glu | Asn | Leu | His | Lys | Pro | Val Ile | |
| | | 125 | | | | 130 | | | | | 135 | | | | |
| CTC | ACT | GGC | GCC | CAG | GTG | CCA | ATC | CGT | GTG | CTG | TGG | AAT | GAC | GCC CGG | 481 |
| Leu | Thr | Gly | Ala | Gln | Val | Pro | Ile | Arg | Val | Leu | Trp | Asn | Asp | Ala Arg | |
| | 140 | | | | 145 | | | | | 150 | | | | | |
| GAA | AAC | CTG | CTG | GGG | GCG | TTG | CTT | GTG | GCC | GGC | CAA | TAC | ATC | ATC CCT | 529 |
| Glu | Asn | Leu | Leu | Gly | Ala | Leu | Leu | Val | Ala | Gly | Gln | Tyr | Ile | Ile Pro | |
| 155 | | | | 160 | | | | | 165 | | | | | 170 | |
| GAG | GTC | TGC | CTG | TTT | ATG | AAC | AGT | CAG | CTG | TTT | CGG | GGA | AAC | CGG GTA | 577 |
| Glu | Val | Cys | Leu | Phe | Met | Asn | Ser | Gln | Leu | Phe | Arg | Gly | Asn | Arg Val | |
| | | | 175 | | | | | 180 | | | | | 185 | | |
| ACC | AAG | GTG | GAC | TCC | CAG | AAG | TTT | GAG | GCC | TTC | TGC | TCC | CCC | AAT CTG | 625 |
| Thr | Lys | Val | Asp | Ser | Gln | Lys | Phe | Glu | Ala | Phe | Cys | Ser | Pro | Asn Leu | |
| | | 190 | | | | | 195 | | | | | 200 | | | |
| TCC | CCA | CTA | GCC | ACT | GTG | GGC | GCG | GAT | GTC | ACA | ATT | GCC | TGG | GAC CTG | 673 |
| Ser | Pro | Leu | Ala | Thr | Val | Gly | Ala | Asp | Val | Thr | Ile | Ala | Trp | Asp Leu | |
| | | 205 | | | | 210 | | | | | 215 | | | | |
| GTG | CGC | AAG | GTC | AAC | TGG | AAG | GAC | CCG | CTG | GTG | GTG | CAC | AGC | AAC ATG | 721 |
| Val | Arg | Lys | Val | Asn | Trp | Lys | Asp | Pro | Leu | Val | Val | His | Ser | Asn Met | |
| | 220 | | | | 225 | | | | | 230 | | | | | |
| GAG | CAC | GAC | GTG | GCA | CTG | CTG | CGC | CTC | TAC | CCT | GGC | ATC | CCG | GCC TCC | 769 |
| Glu | His | Asp | Val | Ala | Leu | Leu | Arg | Leu | Tyr | Pro | Gly | Ile | Pro | Ala Ser | |
| 235 | | | | 240 | | | | | 245 | | | | | 250 | |
| CTG | GTC | CGG | GCA | TTC | CTG | CAG | CCC | CCG | CTC | AAG | GGC | GTG | GTC | CTG GAG | 817 |
| Leu | Val | Arg | Ala | Phe | Leu | Gln | Pro | Pro | Leu | Lys | Gly | Val | Val | Leu Glu | |
| | | | 255 | | | | | 260 | | | | | 265 | | |
| ACC | TTC | GGC | TCT | GGC | AAC | GGG | CCG | AGC | AAG | CCC | GAC | CTG | CTG | CAG GAG | 865 |
| Thr | Phe | Gly | Ser | Gly | Asn | Gly | Pro | Ser | Lys | Pro | Asp | Leu | Leu | Gln Glu | |
| | | 270 | | | | | 275 | | | | | 280 | | | |

-continued

| | | |
|---|---|---|
| TTG CGG GCC GCG GCC CAG CGC GGC CTC ATC ATG GTC AAC TGC AGC CAG<br>Leu Arg Ala Ala Ala Gln Arg Gly Leu Ile Met Val Asn Cys Ser Gln<br>285                        290                        295 | 913 | |
| TGC CTG CGG GGG TCT GTG ACC CCG GGC TAT GCC ACG AGC TTG GCG GGC<br>Cys Leu Arg Gly Ser Val Thr Pro Gly Tyr Ala Thr Ser Leu Ala Gly<br>300                        305                        310 | 961 | |
| GCC AAC ATC GTG TCC GGC TTA GAC ATG ACC TCA GAG GCC GCG CTG GCT<br>Ala Asn Ile Val Ser Gly Leu Asp Met Thr Ser Glu Ala Ala Leu Ala<br>315                        320                        325                        330 | 1009 | |
| AAG CTG TCC TAC GTG TTG GGC CTG CCG GAG CTG AGC CTG GAG CGC AGG<br>Lys Leu Ser Tyr Val Leu Gly Leu Pro Glu Leu Ser Leu Glu Arg Arg<br>                  335                        340                        345 | 1057 | |
| CAG GAG CTG CTG GCC AAG GAT CTT CGC GGG GAA ATG ACA CTG CCC ACG<br>Gln Glu Leu Leu Ala Lys Asp Leu Arg Gly Glu Met Thr Leu Pro Thr<br>                  350                        355                        360 | 1105 | |
| GCA GAC CTG CAC CAG TCC TCT CCG CCG GGC AGC ACA CTG GGG CAA GGT<br>Ala Asp Leu His Gln Ser Ser Pro Pro Gly Ser Thr Leu Gly Gln Gly<br>                  365                        370                        375 | 1153 | |
| GTC GCC CGG CTC TTT AGT CTG TTC GGT TGC CAG GAG GAA GAT TCG GTG<br>Val Ala Arg Leu Phe Ser Leu Phe Gly Cys Gln Glu Glu Asp Ser Val<br>380                        385                        390 | 1201 | |
| CAG GAC GCC GTG ATG CCC AGC CTG GCC CTG GCC TTG GCC CAT GCT GGT<br>Gln Asp Ala Val Met Pro Ser Leu Ala Leu Ala Leu Ala His Ala Gly<br>395                        400                        405                        410 | 1249 | |
| GAA CTC GAG GCT CTG CAG GCA CTT ATG GAG CTG GGC AGT GAC CTG CGC<br>Glu Leu Glu Ala Leu Gln Ala Leu Met Glu Leu Gly Ser Asp Leu Arg<br>                  415                        420                        425 | 1297 | |
| CTA AAG GAC TCT AAT GGC CAA ACC CTG TTG CAT GTG GCT GCT CGG AAT<br>Leu Lys Asp Ser Asn Gly Gln Thr Leu Leu His Val Ala Ala Arg Asn<br>                  430                        435                        440 | 1345 | |
| GGG CGT GAT GGC GTG GTC ACC ATG CTG CTG CAC AGA GGC ATG GAT GTC<br>Gly Arg Asp Gly Val Val Thr Met Leu Leu His Arg Gly Met Asp Val<br>445                        450                        455 | 1393 | |
| AAT GCC CGA GAC CGA GAC GGC CTC AGC CCA CTG CTG TTG GCT GTA CAG<br>Asn Ala Arg Asp Arg Asp Gly Leu Ser Pro Leu Leu Leu Ala Val Gln<br>460                        465                        470 | 1441 | |
| GGC AGG CAT CGG GAA TGC ATC AGG CTG CTG CGG AAG GCT GGG GCC TGC<br>Gly Arg His Arg Glu Cys Ile Arg Leu Leu Arg Lys Ala Gly Ala Cys<br>475                        480                        485                        490 | 1489 | |
| CTG TCC CCC CAG GAC CTG AAG GAT GCA GGG ACC GAG CTG TGC AGG CTG<br>Leu Ser Pro Gln Asp Leu Lys Asp Ala Gly Thr Glu Leu Cys Arg Leu<br>                  495                        500                        505 | 1537 | |
| GCA TCC AGG GCT GAC ATG GAA GGC CTG CAG GCA TGG GGG CAG GCT GGG<br>Ala Ser Arg Ala Asp Met Glu Gly Leu Gln Ala Trp Gly Gln Ala Gly<br>                  510                        515                        520 | 1585 | |
| GCC GAC CTG CAG CAG CCG GGC TAT GAT GGG CGC AGC GCT CTG TGT GTC<br>Ala Asp Leu Gln Gln Pro Gly Tyr Asp Gly Arg Ser Ala Leu Cys Val<br>                  525                        530                        535 | 1633 | |
| GCA GAA GCA GCC GGG AAC CAG GAG GTG CTG GCC CTT CTG CGG AAC CTG<br>Ala Glu Ala Ala Gly Asn Gln Glu Val Leu Ala Leu Leu Arg Asn Leu<br>540                        545                        550 | 1681 | |
| GCA CTT GTA GGC CCG GAA GTG CCG CCT GCC ATC TGATCGCCAG CAATCCCGCT<br>Ala Leu Val Gly Pro Glu Val Pro Pro Ala Ile<br>555                        560                        565 | 1734 | |
| GTGGTGTGAG CCACTCCGCC ATCTGCTGCT TTGACCCACT CGAGGGACCC TAGCACACGA | 1794 | |
| CCCCCCAGCA GGATGCACCC CACTACTTAG AGTATACCCC AGGCTGGCTC AGTGACAAGC | 1854 | |
| TGCAAAGGTC TTTGTTGGCA GAACAGCAAT AAAGTAACTA CAGAGTGGCC AAAAAAAAAA | 1914 | |
| AAAAAAAAAA AAAA | 1928 | |

(2) INFORMATION FOR SEQ ID NO:16:

(i) SEQUENCE CHARACTERISTICS:
        (A) LENGTH:2096 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:human
        (F) TISSUE TYPE:liver (iX) FEATURE:
        (A) NAME/KEY:5'UTR
        (B) LOCATION:1..92
        (C) IDENTIFICATION METHOD:S
        (A) NAME/KEY:mat peptide
        (B) LOCATION:93..1811
        (C) IDENTIFICATION METHOD:S
        (A) NAME/KEY:3'UTR
        (B) LOCATION:1812..2096
        (C) IDENTIFICATION METHOD:S (xi) SEQUENCE DESCRIPTION: SEQ ID NO:16:

```
CGCCCCGGGC CTCCTCCGCG CAGTCCCTGA GTCCCGCAGG CCCTGCGTCC CCGCTGCACA       60

CCCCCGTCCA CTCCCGTGGT CCCCGGTCCG GC ATG GCG CGC GCG GTG GGG CCC        113
                                  Met Ala Arg Ala Val Gly Pro
                                   1               5

GAG CGG AGG CTG CTG GCC GTC TAC ACC GGC GGC ACC ATT GGC ATG CGG        161
Glu Arg Arg Leu Leu Ala Val Tyr Thr Gly Gly Thr Ile Gly Met Arg
         10                  15                  20

AGT GAG CTC GGC GTG CTT GTG CCC GGG ACG GGC CTG GCT GCC ATC CTG        209
Ser Glu Leu Gly Val Leu Val Pro Gly Thr Gly Leu Ala Ala Ile Leu
 25                  30                  35

AGG ACA CTG CCC ATG TTC CAT GAC GAG GAG CAC GCC CGA GCC CGC GGC        257
Arg Thr Leu Pro Met Phe His Asp Glu Glu His Ala Arg Ala Arg Gly
 40                  45                  50                  55

CTC TCT GAG GAC ACC CTG GTG CTA CCC CCG GAC AGC CGC AAC CAG AGG        305
Leu Ser Glu Asp Thr Leu Val Leu Pro Pro Asp Ser Arg Asn Gln Arg
 60                  65                  70

ATC CTC TAC ACC GTG CTG GAG TGC CAG CCC CTC TTC GAC TCC AGT GAC        353
Ile Leu Tyr Thr Val Leu Glu Cys Gln Pro Leu Phe Asp Ser Ser Asp
             75                  80                  85

ATG ACC ATC GCT GAG TGG GTT CGC GTT GCC CAG ACC ATC AAG AGG CAC        401
Met Thr Ile Ala Glu Trp Val Arg Val Ala Gln Thr Ile Lys Arg His
             90                  95                 100

TAC GAG CAG TAC CAC GGC TTT GTG GTC ATC CAC GGC ACC GAC ACC ATG        449
Tyr Glu Gln Tyr His Gly Phe Val Val Ile His Gly Thr Asp Thr Met
        105                 110                 115

GCC TTT GCT GCC TCG ATG CTG TCC TTC ATG CTG GAG AAC CTG CAG AAG        497
Ala Phe Ala Ala Ser Met Leu Ser Phe Met Leu Glu Asn Leu Gln Lys
120                 125                 130                 135

ACT GTC ATC CTC ACT GGG GCC CAG GTG CCC ATC CAT GCC CTG TGG AGC        545
Thr Val Ile Leu Thr Gly Ala Gln Val Pro Ile His Ala Leu Trp Ser
                140                 145                 150

GAC GGC CGT GAG AAC CTG CTG GGG GCA CTG CTC ATG GCT GGC CAG TAT        593
Asp Gly Arg Glu Asn Leu Leu Gly Ala Leu Leu Met Ala Gly Gln Tyr
                155                 160                 165
```

```
GTG ATC CCA GAG GTC TGC CTT TTC TTC CAG AAT CAG CTG TTT CGG GGC      641
Val Ile Pro Glu Val Cys Leu Phe Phe Gln Asn Gln Leu Phe Arg Gly
        170                 175                 180

AAC CGG GCA ACC AAG GTA GAC GCT CGG AGG TTC GCA GCT TTC TGC TCC      689
Asn Arg Ala Thr Lys Val Asp Ala Arg Arg Phe Ala Ala Phe Cys Ser
    185                 190                 195

CCG AAC CTG CTG CCT CTG GCC ACA GTG GGT GCT GAC ATC ACA ATC AAC      737
Pro Asn Leu Leu Pro Leu Ala Thr Val Gly Ala Asp Ile Thr Ile Asn
200                 205                 210                 215

AGG GAG CTG GTG CGG AAG GTG GAC GGG AAG GCT GGG CTG GTG GTG CAC      785
Arg Glu Leu Val Arg Lys Val Asp Gly Lys Ala Gly Leu Val Val His
                220                 225                 230

AGC AGC ATG GAG CAG GAC GTG GGC CTG CTG CGC CTC TAC CCT GGG ATC      833
Ser Ser Met Glu Gln Asp Val Gly Leu Leu Arg Leu Tyr Pro Gly Ile
            235                 240                 245

CCT GCC GCC CTG GTT CGG GCC TTC TTG CAG CCT CCC CTG AAG GGC GTG      881
Pro Ala Ala Leu Val Arg Ala Phe Leu Gln Pro Pro Leu Lys Gly Val
                250                 255                 260

GTC ATG GAG ACC TTC GGT TCA GGG AAC GGA CCC ACC AAG CCC GAC CTG      929
Val Met Glu Thr Phe Gly Ser Gly Asn Gly Pro Thr Lys Pro Asp Leu
        265                 270                 275

CTG CAG GAG CTG CGG GTG GCC ACC GAG CGC GGC CTG GTC ATC GTC AAC      977
Leu Gln Glu Leu Arg Val Ala Thr Glu Arg Gly Leu Val Ile Val Asn
280                 285                 290                 295

TGT ACC CAC TGC CTC CAG GGG GCT GTG ACC ACA GAC TAT GCA GCT GGC     1025
Cys Thr His Cys Leu Gln Gly Ala Val Thr Thr Asp Tyr Ala Ala Gly
                300                 305                 310

ATG GCC ATG GCG GGA GCC GGC GTC ATC TCA GGC TTC GAC ATG ACA TCG     1073
Met Ala Met Ala Gly Ala Gly Val Ile Ser Gly Phe Asp Met Thr Ser
            315                 320                 325

GAG GCC GCC CTG GCC AAG CTA TCG TAT GTG CTG GGC CAG CCA GGG CTG     1121
Glu Ala Ala Leu Ala Lys Leu Ser Tyr Val Leu Gly Gln Pro Gly Leu
                330                 335                 340

AGC CTG GAT GTC AGG AAG GAG CTG CTG ACC AAG GAC CTT CGG GGG GAG     1169
Ser Leu Asp Val Arg Lys Glu Leu Leu Thr Lys Asp Leu Arg Gly Glu
        345                 350                 355

ATG ACG CCA CCC TCG GTG GAA GAG CGC CGG CCC TCA CTG CAG GGC AAC     1217
Met Thr Pro Pro Ser Val Glu Glu Arg Arg Pro Ser Leu Gln Gly Asn
360                 365                 370                 375

ACG CTG GGC GGT GGG GTC TCC TGG CTC CTC AGT CTG AGC GGC AGC CAG     1265
Thr Leu Gly Gly Gly Val Ser Trp Leu Leu Ser Leu Ser Gly Ser Gln
                380                 385                 390

GAG GCA GAT GCC CTG CGG AAT GCC CTG GTG CCC AGC CTG GCC TGT GCT     1313
Glu Ala Asp Ala Leu Arg Asn Ala Leu Val Pro Ser Leu Ala Cys Ala
            395                 400                 405

GCT GCC CAC GCC GGT GAC GTG GAG GCG CTG CAG GCG CTT GTG GAG CTG     1361
Ala Ala His Ala Gly Asp Val Glu Ala Leu Gln Ala Leu Val Glu Leu
                410                 415                 420

GGC AGT GAC CTG GGC CTG GTG GAC TTT AAC GGC CAA ACC CCA CTG CAC     1409
Gly Ser Asp Leu Gly Leu Val Asp Phe Asn Gly Gln Thr Pro Leu His
        425                 430                 435

GCG GCC GCC CGG GGA GGC CAC ACA GAG GCA GTC ACC ATG CTG CTG CAG     1457
Ala Ala Ala Arg Gly Gly His Thr Glu Ala Val Thr Met Leu Leu Gln
440                 445                 450                 455

AGA GGT GTG GAC GTG AAC ACC CGG GAC ACG GAT GGC TTC AGC CCG CTG     1505
Arg Gly Val Asp Val Asn Thr Arg Asp Thr Asp Gly Phe Ser Pro Leu
                460                 465                 470

CTG CTG GCC GTG CGG GGC AGG CAT CCG GGT GTC ATT GGG TTG CTG CGG     1553
Leu Leu Ala Val Arg Gly Arg His Pro Gly Val Ile Gly Leu Leu Arg
            475                 480                 485
```

-continued

```
GAA GCC GGG GCC TCC CTG TCC ACC CAG GAG CTG GAG GAA GCA GGG ACG       1601
Glu Ala Gly Ala Ser Leu Ser Thr Gln Glu Leu Glu Glu Ala Gly Thr
            490                 495                 500

GAG CTG TGC AGG CTG GCA TAC AGG GCC GAC CTC GAA GGC CTG CAG GTG       1649
Glu Leu Cys Arg Leu Ala Tyr Arg Ala Asp Leu Glu Gly Leu Gln Val
        505                 510                 515

TGG TGG CAG GCA GGG GCT GAC CTG GGC CAG CCG GGC TAT GAC GGG CAC       1697
Trp Trp Gln Ala Gly Ala Asp Leu Gly Gln Pro Gly Tyr Asp Gly His
520                 525                 530                 535

AGC GCC CTG CAC GTC GCA GAG GCA GCC GGG AAC CTG GCA GTG GTG GCC       1745
Ser Ala Leu His Val Ala Glu Ala Ala Gly Asn Leu Ala Val Val Ala
                540                 545                 550

TTT CTA CAG AGC CTG GAG GGT GCG GTT GGT GCC CAG GCC CCA TGC CCA       1793
Phe Leu Gln Ser Leu Glu Gly Ala Val Gly Ala Gln Ala Pro Cys Pro
            555                 560                 565

GAA GTG CTG CCT GGT GTC TAACCTGAAG GCGTCCTGCT GCAGTATAAG              1841
Glu Val Leu Pro Gly Val
        570

CCATTCCTTC CTCCCATGAC CTGCTGGAGG GGTCTCAGGC ATGACCCCAC TGCTGGGGCT     1901

GCTTCCCAGC CTGCTCTCAT GTAAAGCCTG AAGGCCTTTG TTGGGCAGGA CGGCAATAAA     1961

GTCTCTGACA TCCCCTCACC AGGTCTGTAC AGCCTGGCTC TGAGAGGCTC TGTCTGGGTC     2021

CGGGACTGTG AAAAAAAAAA AAAAAAAAAA AAAAAAAAAA AAAAAAAAAA AAAAAAAAAA     2081

AAAAAAAAAA AAAAA                                                     2096

(2) INFORMATION FOR SEQ ID NO:17:

(i) SEQUENCE CHARACTERISTICS:
        (A) LENGTH:1695 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:guinea pig
        (F) TISSUE TYPE:liver (iX) FEATURE:
        (A) NAME/KEY:mat peptide
        (B) LOCATION:1..1695

(xi) SEQUENCE DESCRIPTION: SEQ ID NO:17:

ATG GCG CGC GCA TCA GGC TCC GAG AGG CAC CTG CTG CTC ATC TAC ACT       48
Met Ala Arg Ala Ser Gly Ser Glu Arg His Leu Leu Leu Ile Tyr Thr
1               5                   10                  15

GGC GGC ACT TTG GGC ATG CAG AGC AAG GGC GGG GTG CTC GTC CCC GGC       96
Gly Gly Thr Leu Gly Met Gln Ser Lys Gly Gly Val Leu Val Pro Gly
            20                  25                  30

CCA GGC CTG GTC ACT CTG CTG CGG ACC CTG CCC ATG TTC CAT GAC AAG       144
Pro Gly Leu Val Thr Leu Leu Arg Thr Leu Pro Met Phe His Asp Lys
        35                  40                  45

GAG TTC GCC CAG GCC CAG GGC CTC CCT GAC CAT GCT CTG GCG CTG CCC       192
Glu Phe Ala Gln Ala Gln Gly Leu Pro Asp His Ala Leu Ala Leu Pro
    50                  55                  60

CCT GCC AGC CAC GGC CCC AGG GTC CTC TAC ACG GTG CTG GAG TGC CAG       240
Pro Ala Ser His Gly Pro Arg Val Leu Tyr Thr Val Leu Glu Cys Gln
65                  70                  75                  80
```

```
CCC CTC TTG GAT TCC AGC GAC ATG ACC ATC GAT GAT TGG ATT CGC ATA        288
Pro Leu Leu Asp Ser Ser Asp Met Thr Ile Asp Asp Trp Ile Arg Ile
             85                  90                  95

GCC AAG ATC ATA GAG AGG CAC TAT GAG CAG TAC CAA GGC TTT GTG GTT        336
Ala Lys Ile Ile Glu Arg His Tyr Glu Gln Tyr Gln Gly Phe Val Val
                100                 105                 110

ATC CAC GGC ACC GAC ACC ATG GCC TTT GGG GCC TCC ATG CTG TCC TTC        384
Ile His Gly Thr Asp Thr Met Ala Phe Gly Ala Ser Met Leu Ser Phe
            115                 120                 125

ATG CTG GAA AAC CTG CAC AAA CCA GTC ATC CTC ACT GGC GCC CAG GTG        432
Met Leu Glu Asn Leu His Lys Pro Val Ile Leu Thr Gly Ala Gln Val
        130                 135                 140

CCA ATC CGT GTG CTG TGG AAT GAC GCC CGG GAA AAC CTG CTG GGG GCG        480
Pro Ile Arg Val Leu Trp Asn Asp Ala Arg Glu Asn Leu Leu Gly Ala
145                 150                 155                 160

TTG CTT GTG GCC GGC CAA TAC ATC ATC CCT GAG GTC TGC CTG TTT ATG        528
Leu Leu Val Ala Gly Gln Tyr Ile Ile Pro Glu Val Cys Leu Phe Met
                165                 170                 175

AAC AGT CAG CTG TTT CGG GGA AAC CGG GTA ACC AAG GTG GAC TCC CAG        576
Asn Ser Gln Leu Phe Arg Gly Asn Arg Val Thr Lys Val Asp Ser Gln
            180                 185                 190

AAG TTT GAG GCC TTC TGC TCC CCC AAT CTG TCC CCA CTA GCC ACT GTG        624
Lys Phe Glu Ala Phe Cys Ser Pro Asn Leu Ser Pro Leu Ala Thr Val
        195                 200                 205

GGC GCG GAT GTC ACA ATT GCC TGG GAC CTG GTG CGC AAG GTC AAC TGG        672
Gly Ala Asp Val Thr Ile Ala Trp Asp Leu Val Arg Lys Val Asn Trp
    210                 215                 220

AAG GAC CCG CTG GTG GTG CAC AGC AAC ATG GAG CAC GAC GTG GCA CTG        720
Lys Asp Pro Leu Val Val His Ser Asn Met Glu His Asp Val Ala Leu
225                 230                 235                 240

CTG CGC CTC TAC CCT GGC ATC CCG GCC TCC CTG GTC CGG GCA TTC CTG        768
Leu Arg Leu Tyr Pro Gly Ile Pro Ala Ser Leu Val Arg Ala Phe Leu
                245                 250                 255

CAG CCC CCG CTC AAG GGC GTG GTC CTG GAG ACC TTC GGC TCT GGC AAC        816
Gln Pro Pro Leu Lys Gly Val Val Leu Glu Thr Phe Gly Ser Gly Asn
            260                 265                 270

GGG CCG AGC AAG CCC GAC CTG CTG CAG GAG TTG CGG GCC GCG GCC CAG        864
Gly Pro Ser Lys Pro Asp Leu Leu Gln Glu Leu Arg Ala Ala Ala Gln
        275                 280                 285

CGC GGC CTC ATC ATG GTC AAC TGC AGC CAG TGC CTG CGG GGG TCT GTG        912
Arg Gly Leu Ile Met Val Asn Cys Ser Gln Cys Leu Arg Gly Ser Val
    290                 295                 300

ACC CCG GGC TAT GCC ACG AGC TTG GCG GGC GCC AAC ATC GTG TCC GGC        960
Thr Pro Gly Tyr Ala Thr Ser Leu Ala Gly Ala Asn Ile Val Ser Gly
305                 310                 315                 320

TTA GAC ATG ACC TCA GAG GCC GCG CTG GCT AAG CTG TCC TAC GTG TTG       1008
Leu Asp Met Thr Ser Glu Ala Ala Leu Ala Lys Leu Ser Tyr Val Leu
                325                 330                 335

GGC CTG CCG GAG CTG AGC CTG GAG CGC AGG CAG GAG CTG CTG GCC AAG       1056
Gly Leu Pro Glu Leu Ser Leu Glu Arg Arg Gln Glu Leu Leu Ala Lys
            340                 345                 350

GAT CTT CGC GGG GAA ATG ACA CTG CCC ACG GCA GAC CTG CAC CAG TCC       1104
Asp Leu Arg Gly Glu Met Thr Leu Pro Thr Ala Asp Leu His Gln Ser
        355                 360                 365

TCT CCG CCG GGC AGC ACA CTG GGG CAA GGT GTC GCC CGG CTC TTT AGT       1152
Ser Pro Pro Gly Ser Thr Leu Gly Gln Gly Val Ala Arg Leu Phe Ser
    370                 375                 380

CTG TTC GGT TGC CAG GAG GAA GAT TCG GTG CAG GAC GCC GTG ATG CCC       1200
Leu Phe Gly Cys Gln Glu Glu Asp Ser Val Gln Asp Ala Val Met Pro
```

```
                                                                    -continued 385                    390                    395                    400

AGC CTG GCC CTG GCC TTG GCC CAT GCT GGT GAA CTC GAG GCT CTG CAG            1248
Ser Leu Ala Leu Ala Leu Ala His Ala Gly Glu Leu Glu Ala Leu Gln
                405                    410                    415

GCA CTT ATG GAG CTG GGC AGT GAC CTG CGC CTA AAG GAC TCT AAT GGC            1296
Ala Leu Met Glu Leu Gly Ser Asp Leu Arg Leu Lys Asp Ser Asn Gly
                420                    425                    430

CAA ACC CTG TTG CAT GTG GCT GCT CGG AAT GGG CGT GAT GGC GTG GTC            1344
Gln Thr Leu Leu His Val Ala Ala Arg Asn Gly Arg Asp Gly Val Val
                435                    440                    445

ACC ATG CTG CTG CAC AGA GGC ATG GAT GTC AAT GCC CGA GAC CGA GAC            1392
Thr Met Leu Leu His Arg Gly Met Asp Val Asn Ala Arg Asp Arg Asp
    450                    455                    460

GGC CTC AGC CCA CTG CTG TTG GCT GTA CAG GGC AGG CAT CGG GAA TGC            1440
Gly Leu Ser Pro Leu Leu Leu Ala Val Gln Gly Arg His Arg Glu Cys
465                    470                    475                    480

ATC AGG CTG CTG CGG AAG GCT GGG GCC TGC CTG TCC CCC CAG GAC CTG            1488
Ile Arg Leu Leu Arg Lys Ala Gly Ala Cys Leu Ser Pro Gln Asp Leu
                485                    490                    495

AAG GAT GCA GGG ACC GAG CTG TGC AGG CTG GCA TCC AGG GCT GAC ATG            1536
Lys Asp Ala Gly Thr Glu Leu Cys Arg Leu Ala Ser Arg Ala Asp Met
                500                    505                    510

GAA GGC CTG CAG GCA TGG GGG CAG GCT GGG GCC GAC CTG CAG CAG CCG            1584
Glu Gly Leu Gln Ala Trp Gly Gln Ala Gly Ala Asp Leu Gln Gln Pro
                515                    520                    525

GGC TAT GAT GGG CGC AGC GCT CTG TGT GTC GCA GAA GCA GCC GGG AAC            1632
Gly Tyr Asp Gly Arg Ser Ala Leu Cys Val Ala Glu Ala Ala Gly Asn
    530                    535                    540

CAG GAG GTG CTG GCC CTT CTG CGG AAC CTG GCA CTT GTA GGC CCG GAA            1680
Gln Glu Val Leu Ala Leu Leu Arg Asn Leu Ala Leu Val Gly Pro Glu
545                    550                    555                    560

GTG CCG CCT GCC ATC                                                        1695
Val Pro Pro Ala Ile
                565

(2) INFORMATION FOR SEQ ID NO:18:

(i) SEQUENCE CHARACTERISTICS:
        (A) LENGTH:1719 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:human
        (F) TISSUE TYPE:liver (iX) FEATURE:
        (A) NAME/KEY:mat peptide
        (B) LOCATION:1..1719

(xi) SEQUENCE DESCRIPTION: SEQ ID NO:18:

ATG GCG CGC GCG GTG GGG CCC GAG CGG AGG CTG CTG GCC GTC TAC ACC              48
Met Ala Arg Ala Val Gly Pro Glu Arg Arg Leu Leu Ala Val Tyr Thr
1               5                  10                  15

GGC GGC ACC ATT GGC ATG CGG AGT GAG CTC GGC GTG CTT GTG CCC GGG              96
Gly Gly Thr Ile Gly Met Arg Ser Glu Leu Gly Val Leu Val Pro Gly
                20                  25                  30
```

```
ACG GGC CTG GCT GCC ATC CTG AGG ACA CTG CCC ATG TTC CAT GAC GAG       144
Thr Gly Leu Ala Ala Ile Leu Arg Thr Leu Pro Met Phe His Asp Glu
         35                  40                  45

GAG CAC GCC CGA GCC CGC GGC CTC TCT GAG GAC ACC CTG GTG CTA CCC       192
Glu His Ala Arg Ala Arg Gly Leu Ser Glu Asp Thr Leu Val Leu Pro
 50                  55                  60

CCG GAC AGC CGC AAC CAG AGG ATC CTC TAC ACC GTG CTG GAG TGC CAG       240
Pro Asp Ser Arg Asn Gln Arg Ile Leu Tyr Thr Val Leu Glu Cys Gln
 65                  70                  75                  80

CCC CTC TTC GAC TCC AGT GAC ATG ACC ATC GCT GAG TGG GTT CGC GTT       288
Pro Leu Phe Asp Ser Ser Asp Met Thr Ile Ala Glu Trp Val Arg Val
                     85                  90                  95

GCC CAG ACC ATC AAG AGG CAC TAC GAG CAG TAC CAC GGC TTT GTG GTC       336
Ala Gln Thr Ile Lys Arg His Tyr Glu Gln Tyr His Gly Phe Val Val
                 100                 105                 110

ATC CAC GGC ACC GAC ACC ATG GCC TTT GCT GCC TCG ATG CTG TCC TTC       384
Ile His Gly Thr Asp Thr Met Ala Phe Ala Ala Ser Met Leu Ser Phe
             115                 120                 125

ATG CTG GAG AAC CTG CAG AAG ACT GTC ATC CTC ACT GGG GCC CAG GTG       432
Met Leu Glu Asn Leu Gln Lys Thr Val Ile Leu Thr Gly Ala Gln Val
 130                 135                 140

CCC ATC CAT GCC CTG TGG AGC GAC GGC CGT GAG AAC CTG CTG GGG GCA       480
Pro Ile His Ala Leu Trp Ser Asp Gly Arg Glu Asn Leu Leu Gly Ala
145                 150                 155                 160

CTG CTC ATG GCT GGC CAG TAT GTG ATC CCA GAG GTC TGC CTT TTC TTC       528
Leu Leu Met Ala Gly Gln Tyr Val Ile Pro Glu Val Cys Leu Phe Phe
                 165                 170                 175

CAG AAT CAG CTG TTT CGG GGC AAC CGG GCA ACC AAG GTA GAC GCT CGG       576
Gln Asn Gln Leu Phe Arg Gly Asn Arg Ala Thr Lys Val Asp Ala Arg
             180                 185                 190

AGG TTC GCA GCT TTC TGC TCC CCG AAC CTG CTG CCT CTG GCC ACA GTG       624
Arg Phe Ala Ala Phe Cys Ser Pro Asn Leu Leu Pro Leu Ala Thr Val
         195                 200                 205

GGT GCT GAC ATC ACA ATC AAC AGG GAG CTG GTG CGG AAG GTG GAC GGG       672
Gly Ala Asp Ile Thr Ile Asn Arg Glu Leu Val Arg Lys Val Asp Gly
 210                 215                 220

AAG GCT GGG CTG GTG GTG CAC AGC AGC ATG GAG CAG GAC GTG GGC CTG       720
Lys Ala Gly Leu Val Val His Ser Ser Met Glu Gln Asp Val Gly Leu
225                 230                 235                 240

CTG CGC CTC TAC CCT GGG ATC CCT GCC GCC CTG GTT CGG GCC TTC TTG       768
Leu Arg Leu Tyr Pro Gly Ile Pro Ala Ala Leu Val Arg Ala Phe Leu
                 245                 250                 255

CAG CCT CCC CTG AAG GGC GTG GTC ATG GAG ACC TTC GGT TCA GGG AAC       816
Gln Pro Pro Leu Lys Gly Val Val Met Glu Thr Phe Gly Ser Gly Asn
             260                 265                 270

GGA CCC ACC AAG CCC GAC CTG CTG CAG GAG CTG CGG GTG GCC ACC GAG       864
Gly Pro Thr Lys Pro Asp Leu Leu Gln Glu Leu Arg Val Ala Thr Glu
         275                 280                 285

CGC GGC CTG GTC ATC GTC AAC TGT ACC CAC TGC CTC CAG GGG GCT GTG       912
Arg Gly Leu Val Ile Val Asn Cys Thr His Cys Leu Gln Gly Ala Val
 290                 295                 300

ACC ACA GAC TAT GCA GCT GGC ATG GCC ATG GCG GGA GCC GGC GTC ATC       960
Thr Thr Asp Tyr Ala Ala Gly Met Ala Met Ala Gly Ala Gly Val Ile
305                 310                 315                 320

TCA GGC TTC GAC ATG ACA TCG GAG GCC GCC CTG GCC AAG CTA TCG TAT      1008
Ser Gly Phe Asp Met Thr Ser Glu Ala Ala Leu Ala Lys Leu Ser Tyr
                 325                 330                 335

GTG CTG GGC CAG CCA GGG CTG AGC CTG GAT GTC AGG AAG GAG CTG CTG      1056
Val Leu Gly Gln Pro Gly Leu Ser Leu Asp Val Arg Lys Glu Leu Leu
             340                 345                 350
```

```
ACC AAG GAC CTT CGG GGG GAG ATG ACG CCA CCC TCG GTG GAA GAG CGC    1104
Thr Lys Asp Leu Arg Gly Glu Met Thr Pro Pro Ser Val Glu Glu Arg
            355                 360                 365

CGG CCC TCA CTG CAG GGC AAC ACG CTG GGC GGT GGG GTC TCC TGG CTC    1152
Arg Pro Ser Leu Gln Gly Asn Thr Leu Gly Gly Gly Val Ser Trp Leu
        370                 375                 380

CTC AGT CTG AGC GGC AGC CAG GAG GCA GAT GCC CTG CGG AAT GCC CTG    1200
Leu Ser Leu Ser Gly Ser Gln Glu Ala Asp Ala Leu Arg Asn Ala Leu
385                 390                 395                 400

GTG CCC AGC CTG GCC TGT GCT GCT GCC CAC GCC GGT GAC GTG GAG GCG    1248
Val Pro Ser Leu Ala Cys Ala Ala Ala His Ala Gly Asp Val Glu Ala
                405                 410                 415

CTG CAG GCG CTT GTG GAG CTG GGC AGT GAC CTG GGC CTG GTG GAC TTT    1296
Leu Gln Ala Leu Val Glu Leu Gly Ser Asp Leu Gly Leu Val Asp Phe
            420                 425                 430

AAC GGC CAA ACC CCA CTG CAC GCG GCC GCC CGG GGA GGC CAC ACA GAG    1344
Asn Gly Gln Thr Pro Leu His Ala Ala Ala Arg Gly Gly His Thr Glu
        435                 440                 445

GCA GTC ACC ATG CTG CTG CAG AGA GGT GTG GAC GTG AAC ACC CGG GAC    1392
Ala Val Thr Met Leu Leu Gln Arg Gly Val Asp Val Asn Thr Arg Asp
450                 455                 460

ACG GAT GGC TTC AGC CCG CTG CTG CTG GCC GTG CGG GGC AGG CAT CCG    1440
Thr Asp Gly Phe Ser Pro Leu Leu Leu Ala Val Arg Gly Arg His Pro
465                 470                 475                 480

GGT GTC ATT GGG TTG CTG CGG GAA GCC GGG GCC TCC CTG TCC ACC CAG    1488
Gly Val Ile Gly Leu Leu Arg Glu Ala Gly Ala Ser Leu Ser Thr Gln
                485                 490                 495

GAG CTG GAG GAA GCA GGG ACG GAG CTG TGC AGG CTG GCA TAC AGG GCC    1536
Glu Leu Glu Glu Ala Gly Thr Glu Leu Cys Arg Leu Ala Tyr Arg Ala
            500                 505                 510

GAC CTC GAA GGC CTG CAG GTG TGG TGG CAG GCA GGG GCT GAC CTG GGG    1584
Asp Leu Glu Gly Leu Gln Val Trp Trp Gln Ala Gly Ala Asp Leu Gly
        515                 520                 525

CAG CCG GGC TAT GAC GGG CAC AGC GCC CTG CAC GTC GCA GAG GCA GCC    1632
Gln Pro Gly Tyr Asp Gly His Ser Ala Leu His Val Ala Glu Ala Ala
    530                 535                 540

GGG AAC CTG GCA GTG GTG GCC TTT CTA CAG AGC CTG GAG GGT GCG GTT    1680
Gly Asn Leu Ala Val Val Ala Phe Leu Gln Ser Leu Glu Gly Ala Val
545                 550                 555                 560

GGT GCC CAG GCC CCA TGC CCA GAA GTG CTG CCT GGT GTC                1719
Gly Ala Gln Ala Pro Cys Pro Glu Val Leu Pro Gly Val
                565                 570     573
```

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
AATCTCGAGC CACCATGGCG CGCGCATCA                                      29
```

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:20:

CTGCGGCCGC TTATCAGATG GCAGGCGGCA C                                    31

(2) INFORMATION FOR SEQ ID NO:21:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Gly Ser Gly Asn Gly Pro Thr Lys Pro Asp Leu Leu Gln Glu Leu Arg
1               5                   10                  15

Cys (2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

AATCTCGAGC CACCATGGCG CGCGCGGTG                                       29

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CTGCGGCCGC TTATCAGACA CCAGGCAGCA C                                    31

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CTGCGGCCGC TTATCATGCC GTGGGCAGTG T                                    31

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CTGCGGCCGC TTATCAGCCC AACACGTAGG A                                          31

(2) INFORMATION FOR SEQ ID NO:26:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

CTGCGGCCGC TCATTACACC GAGGGTGGCG T                                          31

(2) INFORMATION FOR SEQ ID NO:27:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:27:

CCCCCGGAGG CACTGGGT                                                         18

(2) INFORMATION FOR SEQ ID NO:28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:28:

ACCCAGTGCC TCCGGGGG                                                         18

(2) INFORMATION FOR SEQ ID NO:29:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:29:

CCCCTGGAGG CACTGGGT                                                         18

(2) INFORMATION FOR SEQ ID NO:30:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:30:

ACCCAGTGCC TCCAGGGG                                                        18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CCCCCGGAGG CAGTGGGT                                                        18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

ACCCACTGCC TCCGGGGG                                                        18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GACGTTGGCT CCCGCCAT                                                        18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

ATGGCGGGAG CCAACGTC                                                        18

(2) INFORMATION FOR SEQ ID NO:35:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GCGAATTCAT GGCGCGCGCA TCA                                                  23

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GCAAGCTTTC AGATGGCAGG CGGCAC                                            26

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GTGAATTCGG AGGTTCAGAT GGCGCGCGCA TCA                                    33

(2) INFORMATION FOR SEQ ID NO:38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CTGCGGCCGC TCAGATGGCA GGCGGCAC                                          28

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TCGAGCCACC ATGAAGTGTT CGTGGGTTAT T                                      31

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

TTCTTCCTGA TGGCCGTAGT GACAGGAGTG                                        30

(2) INFORMATION FOR SEQ ID NO:41:

(i) SEQUENCE CHARACTERISTICS:
        (A) LENGTH: 30 base pairs (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:41:

AATTCACTCC TGTCACTACG GCCATCAGGA                                          30

(2) INFORMATION FOR SEQ ID NO:42:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:42:

AGAAAATAAC CCACGAACAC TTCATGGTGG C                                        31

(2) INFORMATION FOR SEQ ID NO:43:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:43:

GCAAGCTTTC ATGCCGTGGG CAGTGT                                              26

(2) INFORMATION FOR SEQ ID NO:44:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:44:

GCGAATTCAT GGCGCGCGCG GTG                                                 23

(2) INFORMATION FOR SEQ ID NO:45:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:45:

GCAAGCTTTC ACACCGAGGG TGGCGT                                              26

(2) INFORMATION FOR SEQ ID NO:46:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:46:

CTGCGGCCGC TCATGCCGTG GGCAGTG        27

(2) INFORMATION FOR SEQ ID NO:47:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:47:

CTGAATTCGG AGGTTCAGAT GGCGCGCGCG GGTG        34

(2) INFORMATION FOR SEQ ID NO:48:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:48:

CTGCGGCCGC TCACACCGAG GGTGGCG        27

(2) INFORMATION FOR SEQ ID NO:49:

(i) SEQUENCE CHARACTERISTICS:
      (A) LENGTH:565 amino acids
      (B) TYPE:amino acid
      (C) STRANDEDNESS: single
      (D) TOPOLOGY:linear (ii) MOLECULE TYPE:peptide (xi) SEQUENCE DESCRIPTION:SEQ ID NO:49:

```
Met Ala Arg Ala Ser Gly Ser Glu Arg His Leu Leu Ile Tyr Thr
1               5                   10                  15

Gly Gly Thr Leu Gly Met Gln Ser Lys Gly Gly Val Leu Val Pro Gly
                20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Phe Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160
```

```
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
            180                 185                 190
Lys Phe Glu Ala Phe Cys Ser Pro Asn Leu Ser Pro Leu Ala Thr Val
        195                 200                 205
Gly Ala Asp Val Thr Ile Ala Trp Asp Leu Val Arg Lys Val Asn Trp
    210                 215                 220
Lys Asp Pro Leu Val Val His Ser Asn Met Glu His Asp Val Ala Leu
225                 230                 235                 240
Leu Arg Leu Tyr Pro Gly Ile Pro Ala Ser Leu Val Arg Ala Phe Leu
                245                 250                 255
Gln Pro Pro Leu Lys Gly Val Val Leu Glu Thr Phe Gly Ser Gly Asn
            260                 265                 270
Gly Pro Ser Lys Pro Asp Leu Leu Gln Glu Leu Arg Ala Ala Ala Gln
        275                 280                 285
Arg Gly Leu Ile Met Val Asn Cys Ser Gln Cys Leu Arg Gly Ser Val
    290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
            340                 345                 350
Asp Leu Arg Gly Glu Met Thr Leu Pro Thr Ala Asp Leu His Gln Ser
        355                 360                 365
Ser Pro Pro Gly Ser Thr Leu Gly Gln Gly Val Ala Arg Leu Phe Ser
    370                 375                 380
Leu Phe Gly Cys Gln Glu Glu Asp Ser Val Gln Asp Ala Val Met Pro
385                 390                 395                 400
Ser Leu Ala Leu Ala Leu Ala His Ala Gly Glu Leu Glu Ala Leu Gln
                405                 410                 415
Ala Leu Met Glu Leu Gly Ser Asp Leu Arg Leu Lys Asp Ser Asn Gly
            420                 425                 430
Gln Thr Leu Leu His Val Ala Ala Arg Asn Gly Arg Asp Gly Val Val
        435                 440                 445
Thr Met Leu Leu His Arg Gly Met Asp Val Asn Ala Arg Asp Arg Asp
    450                 455                 460
Gly Leu Ser Pro Leu Leu Leu Ala Val Gln Gly Arg His Arg Glu Cys
465                 470                 475                 480
Ile Arg Leu Leu Arg Lys Ala Gly Ala Cys Leu Ser Pro Gln Asp Leu
                485                 490                 495
Lys Asp Ala Gly Thr Glu Leu Cys Arg Leu Ala Ser Arg Ala Asp Met
            500                 505                 510
Glu Gly Leu Gln Ala Trp Gly Gln Ala Gly Ala Asp Leu Gln Gln Pro
        515                 520                 525
Gly Tyr Asp Gly Arg Ser Ala Leu Cys Val Ala Glu Ala Ala Gly Asn
    530                 535                 540
Gln Glu Val Leu Ala Leu Leu Arg Asn Leu Ala Leu Val Gly Pro Glu
545                 550                 555                 560
Val Pro Pro Ala Ile
                565
```

-continued (2) INFORMATION FOR SEQ ID NO:50:

(i) SEQUENCE CHARACTERISTICS:
        (A) LENGTH:573 amino acids
        (B) TYPE:amino acid
        (C) STRANDEDNESS: single
        (D) TOPOLOGY:linear (ii) MOLECULE TYPE:peptide (xi) SEQUENCE DESCRIPTION:SEQ ID NO:50:

```
Met Ala Arg Ala Val Gly Pro Glu Arg Arg Leu Leu Ala Val Tyr Thr
 1               5                  10                  15
Gly Gly Thr Ile Gly Met Arg Ser Glu Leu Gly Val Leu Val Pro Gly
                20                  25                  30
Thr Gly Leu Ala Ala Ile Leu Arg Thr Leu Pro Met Phe His Asp Glu
                35                  40                  45
Glu His Ala Arg Ala Arg Gly Leu Ser Glu Asp Thr Leu Val Leu Pro
        50                  55                  60
Pro Asp Ser Arg Asn Gln Arg Ile Leu Tyr Thr Val Leu Glu Cys Gln
 65                  70                  75                  80
Pro Leu Phe Asp Ser Ser Asp Met Thr Ile Ala Glu Trp Val Arg Val
                85                  90                  95
Ala Gln Thr Ile Lys Arg His Tyr Glu Gln Tyr His Gly Phe Val Val
                100                 105                 110
Ile His Gly Thr Asp Thr Met Ala Phe Ala Ala Ser Met Leu Ser Phe
        115                 120                 125
Met Leu Glu Asn Leu Gln Lys Thr Val Ile Leu Thr Gly Ala Gln Val
        130                 135                 140
Pro Ile His Ala Leu Trp Ser Asp Gly Arg Glu Asn Leu Leu Gly Ala
145                 150                 155                 160
Leu Leu Met Ala Gly Gln Tyr Val Ile Pro Glu Val Cys Leu Phe Phe
                165                 170                 175
Gln Asn Gln Leu Phe Arg Gly Asn Arg Ala Thr Lys Val Asp Ala Arg
                180                 185                 190
Arg Phe Ala Ala Phe Cys Ser Pro Asn Leu Leu Pro Leu Ala Thr Val
                195                 200                 205
Gly Ala Asp Ile Thr Ile Asn Arg Glu Leu Val Arg Lys Val Asp Gly
        210                 215                 220
Lys Ala Gly Leu Val Val His Ser Ser Met Glu Gln Asp Val Gly Leu
225                 230                 235                 240
Leu Arg Leu Tyr Pro Gly Ile Pro Ala Ala Leu Val Arg Ala Phe Leu
                245                 250                 255
Gln Pro Pro Leu Lys Gly Val Val Met Glu Thr Phe Gly Ser Gly Asn
                260                 265                 270
Gly Pro Thr Lys Pro Asp Leu Leu Gln Glu Leu Arg Val Ala Thr Glu
        275                 280                 285
Arg Gly Leu Val Ile Val Asn Cys Thr His Cys Leu Gln Gly Ala Val
        290                 295                 300
Thr Thr Asp Tyr Ala Ala Gly Met Ala Met Ala Gly Ala Gly Val Ile
305                 310                 315                 320
Ser Gly Phe Asp Met Thr Ser Glu Ala Ala Leu Ala Lys Leu Ser Tyr
                325                 330                 335
Val Leu Gly Gln Pro Gly Leu Ser Leu Asp Val Arg Lys Glu Leu Leu
                340                 345                 350
Thr Lys Asp Leu Arg Gly Glu Met Thr Pro Pro Ser Val Glu Glu Arg
```

-continued

```
                355                 360                 365
Arg Pro Ser Leu Gln Gly Asn Thr Leu Gly Gly Val Ser Trp Leu
    370                 375                 380

Leu Ser Leu Ser Gly Ser Gln Glu Ala Asp Ala Leu Arg Asn Ala Leu
385                 390                 395                 400

Val Pro Ser Leu Ala Cys Ala Ala Ala His Ala Gly Asp Val Glu Ala
                405                 410                 415

Leu Gln Ala Leu Val Glu Leu Gly Ser Asp Leu Gly Leu Val Asp Phe
                420                 425                 430

Asn Gly Gln Thr Pro Leu His Ala Ala Ala Arg Gly Gly His Thr Glu
            435                 440                 445

Ala Val Thr Met Leu Leu Gln Arg Gly Val Asp Val Asn Thr Arg Asp
    450                 455                 460

Thr Asp Gly Phe Ser Pro Leu Leu Leu Ala Val Arg Gly Arg His Pro
465                 470                 475                 480

Gly Val Ile Gly Leu Leu Arg Glu Ala Gly Ala Ser Leu Ser Thr Gln
                485                 490                 495

Glu Leu Glu Glu Ala Gly Thr Glu Leu Cys Arg Leu Ala Tyr Arg Ala
                500                 505                 510

Asp Leu Glu Gly Leu Gln Val Trp Trp Gln Ala Gly Ala Asp Leu Gly
            515                 520                 525

Gln Pro Gly Tyr Asp Gly His Ser Ala Leu His Val Ala Glu Ala Ala
        530                 535                 540

Gly Asn Leu Ala Val Val Ala Phe Leu Gln Ser Leu Glu Gly Ala Val
545                 550                 555                 560

Gly Ala Gln Ala Pro Cys Pro Glu Val Leu Pro Gly Val
                565                 570         573
```